US007129057B2

(12) United States Patent
Herr et al.

(10) Patent No.: US 7,129,057 B2
(45) Date of Patent: Oct. 31, 2006

(54) HUMAN TESTIS SPECIFIC SERINE/THREONINE KINASE 3

(75) Inventors: John C. Herr, Charlottesville, VA (US); Pablo E. Visconti, Amherst, MA (US); Zhonglin Hao, Charlottesville, VA (US); Gregory S. Kopf, Wynnewood, PA (US)

(73) Assignees: University of Virginia Patent Foundation, Charlottesville, VA (US); The Trustees of the University of Pennsylvania, Philadelphia, PA (US)

( * ) Notice: Subject to any disclaimer, the term of this patent is extended or adjusted under 35 U.S.C. 154(b) by 302 days.

(21) Appl. No.: 10/416,477

(22) PCT Filed: Nov. 9, 2001

(86) PCT No.: PCT/US01/46803

§ 371 (c)(1),
(2), (4) Date: May 9, 2003

(87) PCT Pub. No.: WO02/38732

PCT Pub. Date: May 16, 2002

(65) Prior Publication Data

US 2004/0030112 A1 Feb. 12, 2004

Related U.S. Application Data

(60) Provisional application No. 60/264,921, filed on Jan. 30, 2001, provisional application No. 60/246,939, filed on Nov. 9, 2000.

(51) Int. Cl.
*C12Q 1/48* (2006.01)
*C12N 9/12* (2006.01)
*C07K 1/00* (2006.01)

(52) U.S. Cl. .................... 435/15; 530/350; 435/194
(58) Field of Classification Search ............... 435/194, 435/15, 252.3, 320.1, 6; 530/350
See application file for complete search history.

(56) References Cited

U.S. PATENT DOCUMENTS

2003/0211093 A1* 11/2003 Yue et al. ............... 424/94.5
2004/0048249 A1* 3/2004 Tang et al. ............... 435/6

OTHER PUBLICATIONS

Visconti, P. E., et al., "Cloning and Chromosomal Localization of a Gene Encoding a Novel Serine/Threonine Kinase Belonging to the Subfamily of Testis-Specific Kinases", Genomics, 2001, 77:3:163-170.

Toshima, J., et al., "Identification and Characterization of a Novel Protein Kinase, TESK1, Specifically Expressed in Testicular Germ Cells", Journal of Biological Chemistry, 1995, 270:52:31331-31337.

Herr, J. C., Faculty/Core Leaders University of Virginia, XP002308009 URL:http://web.archive.org/web/20000918171959/hsc.virginia.edu/medicine/basic-sci/cellbio/crgcv/people/jch7k.html>, Oct. 18, 2000, p. 1-2.

Visconti, P. E., et al., "Cholesterol Efflux-Mediated Signal Transduction in Mammalian Sperm: Cholesterol Release Signals an Increase in Protein Tyrosine Phosphorylation during Mouse Sperm Capacitation", Developmental Biology, 1999, 214:429-443.

De Lamirande, Eve, et al., "Capacitation as a regulatory event that primes spermatozoa for the acrosome reaction and fertilization", Molecular Human Reproduction, 1997, 3:3:175-194.

Database Embl, database accession No. AL109945, 1999 Human DNA sequence from clone RP4-811H24 on chromosome 1p34.1-34.3 Contains the 3' end of LCK gene for lymphocyte-specific protein tyrosine kinase, HDAC1 gene for histone deacetylase 1, the MLP gene for MARCKS-like protein STK22C.

Database Embl, database accession No. AC010431, "*Homo sapiens* chromosome 5 clone CTD-2201G3, complete sequence." XP002308771, Sep. 17, 1999.

Database Embl, database accession No. AL359537, "Human DNA sequence*Sequencing Cancelled* from clone RP13-67019" XP002308772, Jun. 18, 2000.

Bielke, W., Blaschke, R. J., Miescher, G. C., Zurcher, G., Andres, A. C., and Ziemiecki, A. (1994). "Characterization of a novel murine testis-specific serine/threonine kinase". Gene. vol. 139, pp. 235-239.

Kueng, P., Nikolova, Z., Djonov, V., Hemphill, A., Rohrbach, V., Boehlen, D., Zuercher, G., Andres, A. C., and Ziemiecki, A. (1997). "A novel family of serine/threonine kinases participating in spermiogenesis". J Cell Biol. vol. 139, pp. 1851-1859.

Visconti, P. E., Bailey, J. L., Moore, G. D., Pan, D., Olds-Clarke, P., and Kopf, G. S. (1995a). "Capacitation of mouse spermatozoa. I. Correlation between the capacitation state and protein tyrosine phosphorylation". Development. vol. 121, pp. 1129-1137.

Visconti, P. E., Johnson, L. R., Oyaski, M., Fornes, M., Moss, S. B., Gerton, G. L., and Kopf, G. S. (1997). "Regulation, localization, and anchoring of protein kinase A subunits during mouse sperm capacitation". Dev. Biol. vol. 192, pp. 351-363.

(Continued)

*Primary Examiner*—Maryam Monshipouri
(74) *Attorney, Agent, or Firm*—Rodney L. Sparks

(57) ABSTRACT

The present invention relates to a family of testis specific kinases (the tssk family), nucleic acid sequences encoding those kinases and antibodies against the kinases. The invention is further directed to the use of thise kinases as targets for isolating specific inhibitors or anagonists of tssk kinase activity. Such inhibitors are anticipated to have use as contraceptive agents.

4 Claims, 1 Drawing Sheet

OTHER PUBLICATIONS

Visconti, P. E., and Kopf, G. S., (1998). "Regulation of protein phosphorylation during sperm capacitation". Biol. Reprod. vol. 59, pp. 1-6.

Visconti, P.E., Moore, G.D., Bailey, J.L., Leclerc, P., Connors, S.A., Pan, D., Olds-Clarke, P., and Kopf, G. S. (1995b). "Capacitation of mouse spermatozoa. II. Protein tyrosine phosphorylation and capacitation are regulated by cAMP-dependent pathway". Development. vol. 121, pp. 1139-1150.

Zuercher, G., Rohrbach, V., Andres, A. C., and Ziemiecki; A. (2000). "A novel member of the testis specific serine kinase family, tssk-3, expressed in the Leydig cells of sexually mature mice". Mech Dev. vol. 93, pp. 175-177.

Database GenEmbl, No. AC010431, Doe Joint Genome Institute and Stanford Human Genome Center. '*Homo sapiens* chromosome 5 clone CTD- 2201G3, complete sequence', Direct Submission, Jun. 8, 2001.

* cited by examiner

Fig. 1

```
TSSK1    MDDAAVLKRR GYLLGINLGE GSYAKVKSAY SERLKFNVAI KIIDRKKAPA DFLEKFLPRE IEILAMLNHC
TSSK2    MDDATVLRKK.GYIVGINLGK GSYAKVKSAY SERLKFNVAV KIIDRKKTPT DFVERFLPRE MDILATVNHG
TSSK3    MED..FLLSN GYQLGKTIGE GTYSKVKEAF SKKHQRKVAI KVIDKMGGPE EFIQRFLPRE LQIVRTLDHK
                                                                                  70

TSSK1    SIIKTYEIFE TSHGKVYIVM ELAVQGDLLE LIKTRGALHE DEARKKFHQL SLAIKYCHDL DVVHRDLKCD
TSSK2    SIIKTYEIFE TSDGRIYIIM ELGVQGDLLE FIKCQGALHE DVARKMFRQL SSAVKYCHDL DIVHRDLKCE
TSSK3    NIIQVYEMLE SADGKICLVM ELAEGGDVFD CVLNGGPLPE SRAKALFRQM VEAIRYCHGC GVAHRDLKCE
                                                                                  140

TSSK1    NLLLDKDFNI KLSDFSFSKR CLRDDSGRMA LSKTFCGSPA YAAPEVLQGI PYQPKVYDIW SLGVILYIMV
TSSK2    NLLLDKDFNI KLSDFGFSKR CLRDSNGRII LSKTFCGSAA YAAPEVLQSI PYQPKVYDIW SLGVILYIMV
TSSK3    NALL.QGFNL KLTDFGFAKV LPKSHRE.... LSQTFCGSTA YAAPEVLQGI PHDSKKKGDVW SMGVLYVML
                                                                                  210

TSSK1    CGSMPYDDSN IKKMLRIQKE HRVNFPRSKH LTGECKDLIY HMLQPDVNRR LHIDEILSHC WMQP.KARGS
TSSK2    CGSMPYDDSD IRKMLRIQKE HRVDFPRSKN LTCECKDLIY RMLQPDVSQR LHIDEILSHS WLQPPKPKAT
TSSK3    CASLPFDDTD IPKMLW.QQQ KGVSFPTHLS ISADCQDLLK RLLEPDMILR PSIEEVSWHP WLAST.....
                                                                                  280

TSSK1    PSVAINKEGE SSRGTEPLWT PEPGSDKKSA TKLEPEGEAQ PQAQPETKPE GTAMQMSRQS EILGFPSKPS
TSSK2    SSASFKREGE GK......YR AECKLDTKTG LRPDHRPDHK VVPENENRME DRLAETSRAK
TSSK3    .......... .......... .......... .......... .......... ..........
                                                                                  350

TSSK1    TMETEEGPPQ QPPETRAQ
TSSK2    DHHISGAEVG KAST.....
TSSK3    .......... ..........
         358
```

HUMAN TESTIS SPECIFIC SERINE/THREONINE KINASE 3

CLAIM TO PRIORITY

This application is a 371 of PCT/US01/46803, filed Nov. 9, 2001, which claims priority to U.S. Provisional Application Ser. No. 60/246,939, filed Nov. 9, 2000 and 60/264,921, filed Jan. 30, 2001, the disclosures of which are incorporated herein.

US GOVERNMENT RIGHTS

This invention was made with United States Government support under Grant Nos. HD 06274, HD 22732, HD 38082, and CA 06927, awarded by National Institutes of Health. The United States Government has certain rights in the invention.

FIELD OF THE INVENTION

The present invention is directed to a family of sperm specific kinases (tssk) genes, their respective encoded proteins and antibodies against those proteins. The present invention also encompasses the use of the tssk kinases as targets for identifying inhibitors of tssk kinase activity.

BACKGROUND OF THE INVENTION

Spermatogenesis, the process in which functional sperm cells are produced in the testis, involves specific interaction between the developing germ cells and their supporting Sertoli cells as well as hormonal regulation by the androgen-producing Leydig cells. The general organization of spermatogenesis is essentially the same in all mammals and can be divided into three distinct phases: 1) The initial phase is the proliferative or spermatogonial phase during which spermatogonia undergo mitotic division and generate a pool of spermatocytes; 2) the meiotic phase, that yields the haploid spermatids; and 3) spermiogenesis whereby each round spermatid differentiates into a spermatozoon. Although the molecular mechanisms regulating the first two phases have been relatively well characterized, the molecular basis of spermiogenesis is largely unknown.

Mammalian spermiogenesis, the postmeiotic phase of spermatogenesis, is characterized by dramatic morphological changes that occur in the haploid spermatid. Some of these changes include the formation of the acrosome and its contents, the condensation and reorganization of the chromatin, the elongation and species-specific reshaping of the cell, and the assembly of the flagellum. These events result from changes in both gene transcription and protein translation that occurs during this developmental period. Some of the proteins translated in the haploid spermatid will remain in the morphologically mature sperm after it leaves the testis. Taking this into consideration, proteins that are synthesized during spermatogenesis might be necessary for spermatid differentiation and/or for sperm function during fertilization.

The present invention relates to signaling events in mammalian sperm that regulate the functions of this highly differentiated cell. More particularly the invention relates to signal transduction that modulates the acquisition of sperm fertilizing capacity. After ejaculation, sperm are able to move actively but lack fertilizing competence. They acquire the ability to fertilize in the female genital tract in a time-dependent process called capacitation. Capacitation has been demonstrated to be accompanied by the protein phosphorylation of several proteins on both serine/threonine and tyrosine residues, and that protein tyrosine phosphorylation is regulated downstream by a cAMP/PKA pathway that involves the crosstalk between these two signaling pathways. With the exception of PKA, the other kinase(s) involved in the regulation of capacitation are still unknown.

Additional protein kinases have been shown to be involved in spermatogenesis, however, only a few of them are exclusively expressed in germ cells or in the testis (Jinno et al, 1993, *Cell Biol* 13, 4146–56; Nayak et al, 1998, *Mech Dev* 74, 171–4; Shalom & Don, 1999, *Mol Reprod Dev* 52, 392–405; Toshima et al, 1998, *Biochem Biophys Res Commun* 249, 107–12; Toshima et al, 1999, *J Biol Chem* 274, 12171–6; Tseng et al, 1998, *DNA Cell Biol* 17, 823–33; Walden & Cowan, 1993, *Mol Cell Biol* 13, 7625–35). Examples of testis-specific kinases are the recently described mouse genes, tssk 1, 2 and 3 (Bielke et al., 1994, *Gene* 139, 235–9; Kueng et al, 1997, *J Cell Biol* 139, 1851–9; Zuercher et al., 2000, *Mech Dev* 93, 175–7). The function of the tssk kinase family is unknown. However, since the members of this family are expressed postmeiotically during spermiogenesis, it is hypothesized that they have a role in germ cell differentiation, or later on in sperm function. Therefore, it is anticipated that compounds that interfere with the function of this kinase family could be utilized as contraceptive agents.

Despite the availability of a range of contraceptive methods, over 50% of pregnancies are unintended worldwide and in the United States. Thus, there is a critical need for contraception that better fits the diverse needs of women and men and takes into consideration different ethnic, cultural and religious values. Except for the use of condoms or vasectomy, the availability of contraceptive methods for men is very limited.

The importance of protein kinases in most physiological processes suggests that inhibition of tssk kinase family activity with a specific drug could inhibit fertilization. In accordance with one aspect of the present invention, the tssk kinase family is used as a target for the development of novel drugs. In particular, the sperm-specific tssk gene products will be used to screen for specific inhibitors of tssk kinase activity and these inhibitors will be used either alone or in conjunction with other contraceptive agents to prevent unintended pregnancies. Advantageously, the unique sequence of the members of the tssk kinase family supports the likelihood of finding specific inhibitors for their activity. Finally, if these kinases remain in the sperm after spermatogenesis and have a role in sperm physiology, design of specific tssk kinase inhibitors could be used both in male and female in order to prevent fertilization.

SUMMARY OF THE INVENTION

The present invention is directed to the human sperm-specific tssk kinase gene family and their corresponding proteins. More particularly, the present invention is directed to the human tssk1, tssk2 and tssk 3 kinases and the use of those kinases to identify agonists or antagonists of tssk kinase activity. The present invention also encompasses antibodies raised against the human tssk1, tssk2 and tssk 3 kinases and the use of these antibodies as diagnostic tools.

BRIEF DESCRIPTION OF THE DRAWINGS

FIG. 1. Comparison between the amino acid sequences of human tssk 1, human tssk 2, and human tssk 3. As seen in FIG. 1 the amino acid sequences between the three proteins diverge near the carboxy terminus.

DETAILED DESCRIPTION OF THE INVENTION

Definitions

In describing and claiming the invention, the following terminology will be used in accordance with the definitions set forth below.

As used herein, "nucleic acid," "DNA," and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

The term "peptide" encompasses a sequence of 3 or more amino acids wherein the amino acids are naturally occurring or synthetic (non-naturally occurring) amino acids. Peptide mimetics include peptides having one or more of the following modifications:

1. peptides wherein one or more of the peptidyl—C(O)NR—linkages (bonds) have been replaced by a non-peptidyl linkage such as a —$CH_2$-carbamate linkage (—$CH_2OC.(O)NR$—), a phosphonate linkage, a —$CH_2$-sulfonamide (—$CH_2$—$S(O)_2NR$—) linkage, a urea (—NHC(O)NH—) linkage, a —$CH_2$-secondary amine linkage, or with an alkylated peptidyl linkage (—C(O)NR—) wherein R is $C_1$–$C_4$ alkyl;
2. peptides wherein the N-terminus is derivatized to a —$NRR_1$ group, to a —NRC(O)R group, to a —NRC(O)OR group, to a —$NRS(O)_2R$ group, to a —NHC(O)NHR group where R and $R_1$ are hydrogen or $C_1$–$C_4$ alkyl with the proviso that R and $R_1$ are not both hydrogen;
3. peptides wherein the C terminus is derivatized to —C(O)$R_2$ where $R_2$ is selected from the group consisting of $C_1$–$C_4$ alkoxy, and —$NR_3R_4$ where $R_3$ and $R_4$ are independently selected from the group consisting of hydrogen and $C_1$–$C_4$ alkyl.

Naturally occurring amino acid residues in peptides are abbreviated as recommended by the IUPAC-IUB Biochemical Nomenclature Commission as follows: Phenylalanine is Phe or F; Leucine is Leu or L; Isoleucine is Ile or I; Methionine is Met or M; Norleucine is Nle; Valine is Vat or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; Glycine is Gly or G, and X is any amino acid. Other naturally occurring amino acids include, by way of example, 4-hydroxyproline, 5-hydroxylysine, and the like.

Synthetic or non-naturally occurring amino acids refer to amino acids which do not naturally occur in vivo but which, nevertheless, can be incorporated into the peptide structures described herein. The resulting "synthetic peptide" contain amino acids other than the 20 naturally occurring, genetically encoded amino acids at one, two, or more positions of the peptides. For instance, naphthylalanine can be substituted for trytophan to facilitate synthesis. Other synthetic amino acids that can be substituted into peptides include L-hydroxypropyl, L-3,4-dihydroxyphenylalanyl, alpha-amino acids such as L-alpha-hydroxylysyl and D-alpha-methylalanyl, L-alpha.-methylalanyl, beta.-amino acids, and isoquinolyl. D amino acids and non-naturally occurring synthetic amino acids can also be incorporated into the peptides. Other derivatives include replacement of the naturally occurring side chains of the 20 genetically encoded amino acids (or any L or D amino acid) with other side chains.

As used herein, the term "conservative amino acid substitution" are defined herein as exchanges within one of the following five groups:
I. Small aliphatic, nonpolar or slightly polar residues:
   Ala, Ser, Thr, Pro, Gly;
II. Polar, negatively charged residues and their amides:
   Asp, Asn, Glu, Gln;
III. Polar, positively charged residues:
   His, Arg, Lys;
IV. Large, aliphatic, nonpolar residues:
   Met Leu, Ile, Val, Cys
V. Large, aromatic residues:
   Phe, Tyr, Trp As used herein, the term "purified" and like terms relate to the isolation of a molecule or compound in a form that is substantially free of contaminants normally associated with the molecule or compound in a native or natural environment.

As used herein, the term "biologically active fragments" or "bioactive fragment" of an tssk polypeptide encompasses natural or synthetic portions of the full-length protein that are capable of specific binding to their natural ligand.

"Operably linked" refers to a juxtaposition wherein the components are configured so as to perform their usual function. For example, control sequences or promoters operably linked to a coding sequence are capable of effecting the expression of the coding sequence.

The term "non-native promoter" as used herein refers to any promoter that has been operably linked to a coding sequence wherein the coding sequence and the promoter are not naturally associated (i.e. a recombinant promoter/coding sequence construct).

As used herein, a transgenic cell is any cell that comprises a nucleic acid sequence that has been introduced into the cell in a manner that allows expression of the a gene encoded by the introduced nucleic acid sequence.

The Invention

The present invention is directed to a family of kinases (the tssk kinase family) that are expressed exclusively in germ cells of humans and mice. The mouse homologs of the human tssk genes were previously described and were found to be expressed postmeiotically in male germ cells. (Bielke et al., 1994, *Gene* 139, 235–9; Kueng et al., 1997, *J Cell Biol* 139, 1851–9) Using a combination of two yeast hybrid technology and coimmunoprecipitation, Kueng et al. (1997) found that mouse tssk 1 and 2 bind and phosphorylate a protein of 54 Kda, that represents the tssk substrate. This tssk substrate has been designated tsks. The tsks protein is also testis-specific and its developmental expression suggests that it is postmeiotically expressed in germ cell. The mouse cDNA sequence of the tssk substrate was previously reported (Kueng et al., 1997) and was used to search the EST data base. A human EST homologue AL041339 was found and used to generate sense and antisense primers for obtaining the full length clone by 5' and 3' RACE using human testis marathon ready cDNA (Clontech, Inc.). The full length nucleotide sequence of human tsks is provided as SEQ ID NO: 7 and the deduced protein sequences is provided as SEQ ID NO: 8.

The developmental expression pattern of the tssk kinases, as well as the general relevance of kinases in physiological processes led applicants to believe that this family of testis-specific kinases has a role in spermatogenesis. The finding that the tssk kinase family and one of the putative substrates are expressed at the same time during spermatogenesis is relevant to the potential use of these proteins as contraceptive targets. Accordingly, one aspect of the present invention is directed to the isolation of the human tssk homologs and their use in isolating contraceptive agents.

Since sperm are transcriptionally and translationally inactive, cloning and characterizing candidate sperm protein kinases at the molecular level, requires the use of RNA isolated from male germ cells. RNA transcripts expressed in the male germ cell lineage might ultimately be important in sperm function; however, it is also possible that such transcripts function during testicular spermatogenesis. Using this methodology a unique cDNA was cloned from mouse male germ cells that encodes a putative protein kinase of the ser/thr protein kinase subfamily. That kinase (tssk3b) is specifically expressed postmeiotically in murine male germ cells. In accordance with one embodiment of the present invention a unique testis-specific mouse tssk gene is provided. The nucleic acid sequence and amino acid sequence of tssk3b is provided as SEQ ID NO 10 and SEQ ID NO: 9, respectively.

The human homologue of tssk3b has also been cloned (and designated human tssk3) and exhibits 98% homology to the putative mouse protein at the protein level. The nucleotide sequence and amino acid sequence of human tssk3 is provided as SEQ ID NO 3 and SEQ ID NO: 6, respectively. Recently, a similar mouse protein kinase was described and identified as a testis-specific serine kinase 3 (mouse tssk3) (Zuercher et al., 2000, *Mech Dev* 93, 175–7), a member of a small family of testis-specific protein kinases (Bielke et al., 1994, *Gene* 139, 235–9; Kueng et al., 1997, *J Cell Biol* 139, 1851–9). Despite this homology, both the human tssk3 and the mouse tssk3b cDNAs cloned and described in the present application demonstrate differences with mouse tssk3 in several amino acids.

Using the predicted mouse tssk 1 and 2 amino acid sequences (as described by Kueng et al., 1997) for the purposes of searching the gene bank, a genome sequence of both mouse tssk 1 and tssk2 was obtained. The 3' end and 5' end of the coding region of these genomic mouse genes were then used to design sense and antisense primers, respectively, and used to isolate the human homologs using PCR technology (see Example 2). The amplified cDNA fragments were cloned using the TOPO TA cloning kit (Invitrogen) and sequenced. An amplified human tssk1 gene was approximately 1.3 kb in size and the isolated human tssk 2 gene was approximately 1.2 kb in size. The nucleic acid sequence and amino acid sequence of human tssk1 is provided as SEQ ID NO: 1 and SEQ ID NO: 4, respectively. The nucleic acid sequence and amino acid sequence of human tssk2 is provided as SEQ ID NO: 2 and SEQ ID NO: 5, respectively.

In accordance with one embodiment of the present invention a purified polypeptide is provided comprising the amino acid sequence of SEQ ID NO: 4, SEQ ID NO: 5, SEQ ID NO: 6 or SEQ ID NO: 9, or an amino acid sequence that differs from SEQ ID NO: 4 or SEQ ID NO: 6 by one or more conservative amino acid substitutions. More preferably the purified polypeptide comprises an amino acid sequence that differs from SEQ ID NO: 4 or SEQ ID NO: 6 by less than 5 conservative amino acid substitutions, and more preferably by 2 or less conservative amino acid substitutions.

In one preferred embodiment the purified polypeptide comprises the amino acid sequence of SEQ ID NO: 4, SEQ ID NO: 5 or SEQ ID NO: 6. These polypeptides may include additional amino acid sequences to assist in the purification of recombinantly produced polypeptides. In one embodiment, the purified polypeptide comprises an amino acid sequence selected from the group consisting of SEQ ID NO: 4, SEQ ID NO: 5 and SEQ ID NO: 6 and a peptide tag, wherein the peptide tag is linked to the tssk peptide sequence. Suitable expression vectors for expressing such fusion proteins and suitable peptide tags are known to those skilled in the art and commercially available. In one embodiment the tag comprises a His tag (see Example 4). In another embodiment the purified polypeptide comprises the amino acid sequence of SEQ ID NO: 8 or the amino acid sequence of SEQ ID NO: 8 linked to a peptide tag.

In another embodiment, the present invention is directed to a purified polypeptide that comprises a portion of a tssk polypeptide. More particularly the tssk polypeptide portion consists of natural or synthetic portions of a full-length polypeptide selected from the group consisting of SEQ ID NO: 4, SEQ ID NO: 5, SEQ ID NO: 6 and SEQ ID NO: 9 that are capable of specific binding to their natural ligand. In one embodiment the human tssk fragment retains its ability to bind to tsks.

The present invention also encompasses nucleic acid sequences that encode human tssk. In one embodiment a nucleic acid sequence is provided comprising the sequence of SEQ ID NO: 1, SEQ. ID NO: 2, SEQ ID NO: 3, SEQ ID NO: 10 or fragments thereof. In another embodiment a purified nucleic acid sequence is provided, selected from the group consisting of SEQ ID NO: 1, SEQ ID NO: 2 and SEQ ID NO: 3.

The present invention also includes nucleic acids that hybridize under stringent or highly stringent conditions (as defined herein) to all or a portion of the nucleotide sequence represented by SEQ ID NO: 1, SEQ ID NO: 2, SEQ ID NO: 3 or SEQ ID NO: 10, or their complements. The hybridizing portion of the hybridizing nucleic acids is typically at least 15 (e.g., 20, 25, 30, or 50) nucleotides in length. Hybridizing nucleic acids of the type described herein can be used, for example, as a cloning probe, a primer (e.g., a PCR primer), or a diagnostic probe to detect the expression of the human tssk gene.

Nucleic acid duplex or hybrid stability is expressed as the melting temperature or Tm, which is the temperature at which a nucleic acid duplex dissociates into its component single stranded DNAs. This melting temperature is used to define the required stringency conditions. Typically a 1% mismatch results in a 1° C. decrease in the Tm, and the temperature of the final wash in the hybridization reaction is reduced accordingly (for example, if two sequences having >95% identity, the final wash temperature is decreased from the Tm by 5° C.). In practice, the change in Tm can be between 0.5° C. and 1.5° C. per 1% mismatch.

In one embodiment, the present invention is directed to the nucleic acid sequence of SEQ ID NO: 1, SEQ ID NO: 2 or SEQ ID NO: 3 and nucleic acid sequences that hybridize to those sequences (or their complement) under stringent or highly stringent conditions. In accordance with the present invention highly stringent conditions are defined as conducting the hybridization and wash conditions at no lower than −5° C. Tm. Stringent conditions are defined as involve hybridizing at 68° C. in 5×SSC/5× Denhardt's solution/1.0% SDS, and washing in 0.2×SSC/0.1% SDS at 68° C. Moderately stringent conditions include hybridizing at 68° C. in 5×SSC/5× Denhardt's solution/1.0% SDS and washing in 3×SSC/0.1% SDS at 42° C. Additional guidance regarding such conditions is readily available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

The present invention is also directed to recombinant human tssk gene constructs. In one embodiment, the recombinant gene construct comprises a non-native promoter operably linked to a nucleic acid sequence selected from the group consisting of SEQ ID NO: 1, SEQ ID NO: 2, SEQ ID NO: 3, SEQ ID NO: 7 and SEQ ID NO: 10. In one embodiment the recombinant gene construct comprises a non-native promoter operably linked to a nucleic acid sequence selected from the group consisting of SEQ ID NO: 1, SEQ ID NO: 2 and SEQ ID NO: 3. The non-native promoter is preferably a strong constitutive promoter that allows for expression in a predetermined host cell. These recombinant gene constructs can be introduced into host cells to produce transgenic cell lines that synthesize the tssk gene products. Host cells can be selected from a wide variety of eukaryotic and prokaryotic organisms, and two preferred host cells are E. coli and yeast cells.

In accordance with one embodiment, a nucleic acid sequence selected from the group consisting of SEQ ID NO: 1, SEQ ID NO: 2, SEQ ID NO: 3 and SEQ ID NO: 10 are inserted into a eukaryotic or prokaryotic expression vector in a manner that operably links the gene sequences to the appropriate regulatory sequences, and human tssk is expressed in the appropriate eukaryotic or prokaryotic cells host cell. Suitable eukaryotic host cells and vectors are known to those skilled in the art. The baculovirus system is also suitable for producing transgenic cells and synthesizing the tssk genes of the present invention. One aspect of the present invention is directed to transgenic cell lines that contain recombinant genes that express human tssk and fragments of the human tssk coding sequence. As used herein a transgenic cell is any cell that comprises an exogenously introduced nucleic acid sequence. More preferably the introduced nucleic acid is sufficiently stable in the transgenic cell (i.e. incorporated into the cell's genome, or present in a high copy plasmid) to be passed on to progeny cells. In one embodiment the transgenic cell is a human cell and comprises a nucleic acid sequence selected from the group consisting of SEQ ID NO: 1, SEQ ID NO: 2, SEQ ID NO: 3, SEQ ID NO: 7 and SEQ ID NO: 10. More preferably the nucleic acid sequence is selected from the group consisting of SEQ ID NO: 1, SEQ ID NO: 2 and SEQ ID NO: 3. The present invention also includes non-human transgenic organisms wherein one or more of the cells of the transgenic organism comprise a recombinant gene that expresses the human tssk.

The present invention also encompasses a method for producing human tssk. The method comprises the steps of introducing a nucleic acid sequence comprising sequences encoding the human tssk into a host cell, and culturing the host cell under conditions that allow for expression of the introduced human tssk gene. In one embodiment the promoter is a conditional or inducible promoter, alternatively the promoter may be a tissue specific or temporal restricted promoter (i.e. operably linked genes are only expressed in a specific tissue or at a specific time). The synthesized tssk can be purified using standard techniques and used in high throughput sceeens to identify inhibitors of tssk activity. Alternatively, in one embodiment the recombinantly produced tssk polypeptides, or fragments thereof are used to generate antibodies against the tssk polypeptides. The recombinanatly produced tssks are also used to obtain crystal structures. Such structures would allow for crystallography analysis that would lead to the design of specific drugs to inhibit tssk function.

Preferably, the nucleic acid sequences encoding the sperm-specific kinase are inserted into a suitable expression vector in a manner that operably links the gene sequences to the appropriate regulatory sequences for expression in the preselected host cell. Suitable host cells, vectors and methods of introducing the DNA constructs into cells are known to those skilled in the art. In particular, nucleic acid sequences encoding the sperm-specific kinase may be added to a cell or cells in vitro or in vivo using delivery mechanisms such as liposomes, viral based vectors, or microinjection.

In accordance with one embodiment a composition is provided comprising a peptide having the sequence selected from the group consisting of SEQ ID NO: 4, SEQ ID NO: 5 and SEQ ID NO: 6 or an antigenic fragment thereof. In one embodiment the antigenic fragment consists of the sequence of SEQ ID NO: 4 or SEQ ID NO: 6. The compositions can be combined with a pharmaceutically acceptable carrier or adjuvants and administered to a mammalian species to induce an immune response.

Another embodiment of the present invention is directed to the isolated antibodies that are generated against human tssk or fragments thereof. Antibodies to human tssk may be generated using methods that are well known in the art. In accordance with one embodiment an antibody is provided that specifically binds to a polypeptide selected from the group consisting of SEQ ID NO: 4, SEQ ID NO: 5, SEQ ID NO: 6, SEQ ID NO: 8 and SEQ ID NO: 9. In one embodiment antibodies are provided that bind to a polypeptide selected from the group consisting of SEQ ID NO: 4, SEQ ID NO: 5 and SEQ ID NO: 6. In one preferred embodiment the antibody is a monoclonal antibody. The antibodies may be used with or without modification, and may be labeled by joining them, either covalently or non-covalently, with a reporter molecule. In addition, the antibodies can be formulated with standard carriers and optionally labeled to prepare therapeutic or diagnostic compositions.

The present invention also provides a method for detecting the presence of human tssk. The method comprises the steps of contacting a sample with a labeled antibody that specifically binds to human tssk, removing unbound and non-specific bond material and detecting the presence of the labeled antibody. In one embodiment the labeled compound comprises an antibody that is labeled directly or indirectly (i.e. via a labeled secondary antibody). In particular, the tssk antibodies of the present invention can be used to confirm the expression of tssk as well as its cellular location, or in assays to monitor patients being treated with human soluble tssk or inhibitors.

In accordance with one aspect of the present invention, the tssk kinase family is used as a target for the development of novel drugs. Progress in the field of small molecule library generation using combinatorial chemistry methods coupled to high-throughput screening has accelerated the search for ideal cell-permeable inhibitors. In addition, structural-based design using crystallographic methods has improved the ability to characterize in detail ligand-protein interaction sites that can be exploited for ligand design.

In one embodiment, the present invention provides methods of screening for agents, small molecules, or proteins that interact with polypeptides comprising the sequence of tssk1, tssk2, tssk3 or bioactive fragments thereof. As used herein, the term "biologically active fragments" or "bioactive fragment" of tssk1, tssk2, tssk3 encompasses natural or synthetic portions of the native peptides that are capable of specific binding to at least one of the natural ligands of the respective native tssk1, tssk2, tssk3 polypeptide, including tsks. The invention encompasses both in vivo and in vitro assays to screen small molecules, compounds, recombinant proteins, peptides, nucleic acids, antibodies etc. which bind to or modulate the activity of tssk1, tssk2, tssk3 and are thus useful as therapeutics or diagnostic markers for fertility.

In one embodiment of the present invention tssk polypeptides, selected from the group consisting of SEQ ID NO: 4, SEQ ID NO: 5, SEQ ID NO: 6 and SEQ ID NO: 9, are used to isolate ligands that bind to tssk under physiological conditions. The method comprises the steps of contacting the tssk polypeptides with a mixture of compounds under physiological conditions, removing unbound and non-specifically bound material, and isolating the compounds that remain bound to the tssk polypeptides. Typically, the tssk polypeptides will be bound to a solid support, using standard techniques, to allow for rapid screening of compounds. The solid support can be selected from any surface that has been used to immobilize biological compounds and includes but is not limited to polystyrene, agarose, silica or nitrocellulose. In one embodiment the solid surface comprises functionalized silica or agarose beads. Screening for such compounds can be accomplished using libraries of pharmaceutical agents and standard techniques known to the skilled practitioner.

Ligands that bind to the tssk polypeptides can then be further analyzed for agonists and antagonists activity through the use of an in vitro kinase assay as described in Example 7. Inhibitors of tssk kinase activity have potential use as agents that prevent maturation/capacitation of sperm. Such inhibitors can be formulated as pharmaceutical compositions and administered to a subject to block spermatogenesis and provide a means for contraception.

In accordance with one embodiment, specific inhibitors of the human tssk kinase activity are identified through the use of an in vitro kinase assay that is capable to detecting phosphorylation events. In one embodiment the method of identifying inhibitors of tssk kinase activity comprises combining a labeled source of phosphate with one or more of the human tssk polypeptides in the presence of one or more potential inhibitory compounds. As described in Example 4 the tssk proteins have the property to become autophosphorylated. Therefore by comparing the rate of autophosphorylation that occurs in the presence and absence of the candidate inhibitory compound, specific inhibitory compounds can be identified. In one preferred embodiment a tssk substrate is provided and the assay is based on measuring the rate of phosphorylation of said substrate in the presence and absence of the candidate inhibitory compounds. Preferably large numbers of compounds will screened using high through put techniques to identify tssk specific inhibitory compounds.

In accordance with one embodiment specific inhibitors of the tssk kinase activity are identified by providing an in vitro kinase assay composition, wherein the composition comprises a labeled source of phosphate, a tssk substrate and a tssk kinase selected from the group consisting of SEQ ID NO: 4, SEQ ID NO: 5, SEQ ID NO: 6 and SEQ ID NO: 9. The rate of tssk substrate phosphorylation will be determined under controlled conditions in the absence of any inhibitory compounds, and then the identical conditions will be used to measure the rate of phosphorylation of the tssk substrate when the assay is run in the presence of one or more potential inhibitory compounds. Those compounds that decrease the activity of the tssk kinase will be identified and tested to determine if the inhibitory effect is specific to the tssk kinase.

In one embodiment the method for identifying human tssk inhibitors comprises the steps of providing a labeled source of phosphate, a tssk substrate and a tssk kinase selected from the group consisting of SEQ ID NO: 4, SEQ ID NO: 5, SEQ ID NO: 6, contacting that composition with one or more potential inhibitory compounds and measuring the rate of phosphorylation. In one preferred embodiment the labeled source of phosphate is [γ32P] ATP and the tssk substrate comprises an amino acid sequence of SEQ ID NO: 8. The kinase assay can also be conducted with two or more of the human tssk kinases present to confirm the activity of the inhibitor to all three kinases.

EXAMPLE 1

Isolation of a Novel Mouse Testis Specific Serine/Threonine Kinase

Reverse transcription-polymerase chain reaction (RT-PCR) using degenerate oligonucleotides corresponding to conserved regions present in protein kinases resulted in the isolation of a novel member of the testis-specific serine/threonine kinase. This PCR fragment recognized a 1020 bp transcript in male germ cells by northern blot analysis. Using this fragment as a probe, a full length cDNA was cloned from a mouse mixed germ cell cDNA library. This cDNA has an open reading frame of 804 bases encoding a protein of 268 amino acids. Tissue expression analysis revealed that this protein kinase is developmentally expressed in mouse testicular germ cells and is not present in brain, ovary, kidney, liver or early embryonic cells.

This novel putative serine/threonine protein kinase (SEQ ID NO: 9) is almost identical to tssk3 (Zuercher et al., 2000, *Mech Dev* 93, 175–7), a recently described mouse testis-specific protein kinase, with the exception of several base pair deletions that result in a shift in the coding region and an alteration of 22 amino acids (residues 109 to 131). The human homologue of this novel protein kinase (SEQ ID NO: 6) was subsequently cloned and displayed expression exclusively in the testis. Fluorescence in situ hybridization (FISH) using both the human and mouse cDNA clones revealed syntenic localization on chromosomes 1p34–35 and 4E, respectively. Due to the homology with tssk3 this novel protein kinase is named tssk3b.

Materials and Methods

Isolation of Spermatogenic Cell Populations

Purified populations of pachytene spermatocytes, round spermatids, and condensing spermatids were prepared from decapsulated testes of adult mice (CD-1; Charles Rivers) by sequential dissociation with collagenase and trypsin-DNase 1 (Bellve et al., 1977; Romrell et al., 1976). The cells were separated into discrete populations by sedimentation velocity at unit gravity in 2–4% BSA gradients in enriched Krebs Ringer Bicarbonate Medium (EKRB) (Bellve et al., 1977; Romrell et al., 1976). The pachytene spermatocyte and round spermatid populations were each at least 85% pure, while the condensing spermatid population was ~40–50% pure (contaminated primarily with anucleated residual bodies and some round spermatids).

RNA Isolation and Northern Blot Analysis

Total RNA from somatic tissues, testis of mice of defined ages, and isolated spermatogenic cells of adult mice was isolated by homogenizing the cells in 5 M guanidium isothiocyanate, 25 mM sodium citrate, pH 7.2, 0.5% Sarkosyl, and 0.1 M 2-mercaptoethanol (Chirgwin et al., 1979). Lysates were centrifuged over cushions of 5.7 M CsCl, 0.1 M EDTA at 114,000×g at 20° C. overnight. Pellets were resuspended and extracted with phenol:chloroform, and the RNA was precipitated with ethanol. The integrity of the RNA was verified by ethidium bromide staining of the ribosomal RNA on 1% agarose gels. Equivalent amounts of RNA were subjected to electrophoresis in 1.2% agarose gels containing formaldehyde (Sambrook et al., 1989). RNA was transferred to nitrocellulose paper, baked at 80° C. for 2 hr, and prehybridized in 50% formamide, 5× Denhartdt's, 0.1% SDS, 100 µg/ml Torula RNA, 5×SSPE for a minimum of 1 hr at 42° C. The appropriate DNA probe was generated by PCR, radiolabeled with 32p-dCTP by the random-primed method and incubated with the blots ($1\times10^6$ cpm/ml) in 50% formamide, 5× Denhartdt's, 0.1% SDS, 100 µg/ml Torula RNA, 5×SSPE with 10% dextran sulfate and hybridized at 42° C. overnight. Blots were washed in 2×SSPE, 0.1% SDS and then in 0.1×SSPE, 0.1% SDS, both for 2×10 min at room temperature. After washing, the filters were air-dried and exposed to film at −70° C. with intensifying screens. Northern blots of human tissues were acquired from Clontech and hybridization was performed as described above.

Reverse Transcription-Polymerase Chain Reaction

Reverse transcription-polymerase chain reaction (RT-PCR) was performed using Superscript II from Gibco-BRL according to the manufacturer's instructions, followed by the use of Taq Polymerase from Promega. The PCR conditions were as follows: 1 cycle of 2 min. at 95° C.; 35 cycles of 1 min. at 95° C., 1 min at 55° C. and 1 min at 72° C.; the cycles were finished with 1 cycle of 7 min at 72° C. and then chilled to 4° C. The DNA products were then analyzed on 2% agarose gels. The following degenerate primers were used to target conserved regions of tyrosine kinases: for the reverse transcription step, a degenerate antisense 20-mer corresponding to the coding subregion IX common to the subfamily of tyrosine kinases with the addition of a 5' Eco RI consensus site for subcloning after three random nucleotides (CGTGGATCCA(A/T)AGGACCA(C/G)AC(A/G)TC; SEQ ID NO: 11); (2) For the PCR step the same primer was used together with a degenerate sense 20-mer corresponding to the subregion VIb common to the subfamily of tyrosine kinases, also a consensus site for Eco RI was introduced after four random nucleotides ATTCGGATC-CAC(A/C)G(A/C/T/G)GA(C/T)(C/T)T; SEQ ID NO: 12). After the PCR reaction was completed and the products analyzed, the cDNA was subcloned into a TOPO TA cloning vector according to the manufacturers instructions (In Vitrogen), the Eco RI subcloning consensus sites were not used. Minipreps from 35 positive colonies were prepared using a Qiagen kit and then sequenced using a T7 primer.

Cloning of Mouse tssk 3b

To clone tssk 3b, the unique sequence obtained by RT-PCR was used to design specific primers against this novel kinase. Primers A2 (antisense: CATCACCTTTCTTGCTAT-CATGG; SEQ ID NO: 13) and S2 (sense:(TGT-GAGAACGCCTTGTTGCAG; SEQ ID NO: 14) were used to obtained a PCR fragment of 169 bases. This PCR fragment was subsequently radiolabeled with 32p-dCTP by the random-primed method and used as a probe to screen a oligo-dT primed mixed germ cell cDNA library as previously described.

Cloning of the Human tssk3b Homologue

Using the predicted mouse tssk3b amino acid sequence for the purposes of searching the human EST database, entry AI 553938 was pulled out in a BLAST search. This EST-sequence was used to design an antisense primer A3 (GA-CATCACCTTTTTTGCTATCGT; SEQ ID NO: 15). This primer and an adaptor primer (CCATCCTAATACGACT-CACTATAGGGC; SEQ ID NO: 16) were used in 5' RACE using human testis marathon ready cDNA as the template (Clontech, Inc). The PCR reaction mix was first heated for 10 min at 94° C. and the mix then subjected to 40 cycles of PCR under the following condition: 94° C. 30 sec, 55° C. 30 sec, 72° C. 2 min. Following these cycles, the mix was incubated at 72° C. for 10 min. AmpTaq Gold (Perkin Elmer) was used in place of conventional Taq polymerase for the PCR. The amplified cDNA fragment was cloned and sequenced using the TOPO TA cloning kit (Invitrogen). The 5' end of the cDNA sequence obtained following 5' RACE was used to design a sense primer S3 (GCAGGTGAGAAT-GTTCTAACGCTG; SEQ ID NO: 17); an antisense primer A4 (TCTCCCCCTACTTTATTGGAGAGC; SEQ ID NO: 18) was based on the 3' end of AI 553938. These two primers were then used to amplify the full length human tssk3b homologue from the same library using the conditions described above. The amplified 1.058 kb fragment was excised, cloned and sequenced using the University of Virginia sequencing facility. A C-terminal 400 bp fragment of the cDNA library amplified tssk3b human homologue was used for northern blots of human tissues.

DNA Sequencing and Computer Analysis

All sequencing was performed with the AmpliTaq, FS dye terminator cycle sequencing kit chemistry and the appropriate primers using a 373A DNA sequencer (PE Applied Biosystems, Foster City, Calif.). Ambiguities were resolved by sequencing the opposite strand. DNA and protein sequence analyses were performed using the MacVectorTM (Kodak Scientific Imaging Systems, New Haven, Conn.) and SequencherTM (Gene Codes Corp., Ann Arbor, Mich.) software programs.

Fluorescence In Situ Hybridization and Chromosomal Mapping

Fluorescence in situ hybridization (FISH) and detection of immunofluorescence were carried out as previously described (Bell et al., 1995, *Cytogenet. Cell Genet*, 70: 263–267). The 1 kb, mouse cDNA clone, as well as the corresponding 1 kb human homologue, were biotinylated by nick translation in a reaction containing 1 µg DNA, 20 µM each of dA TP, dCTP and dGTP (Perkin Elmer), 1 µM dTTP (Perkin Elmer), 25 mM Tris-HCl, pH 7.5,5 mM MgCl2 (Sigma), 10 mM B-mercaptoethanol (Sigma), 10 µM biotin-16-dUTP (Boehringer Mannheim), 2 units DNA polymerase I/DNase I (GIBCO, BRL), and $H_2O$ to a total volume of 50 µl. Probes were denatured and hybridized to metaphase spreads from human peripheral lymphocytes and mouse embryonic fibroblasts, respectively. The hybridized probe was detected with fluorescein-labeled avidin and the signal amplified by the addition of anti-avidin antibody (Oncor) and a second layer of fluorescein-labeled avidin. The chromosome preparations were counterstained with DAPI and observed with a Zeiss Axiophot epiflourescence microscope equipped with a cooled CCD camera (Photometrics, Tucson, Ariz.) operated by a Macintosh computer workstation. Digitized images of DAPI staining and FITC signals were captured, pseudocolored, and merged using Oncor version 1.6 software.

Results

Cloning of Protein Kinases from Murine Male Germ Cells

Mammalian sperm capacitation is accompanied by an increase in protein tyrosine phosphorylation of several proteins. Since mature sperm are not able to synthesize proteins and the presence of RNA in these cells is controversial, in order to identify protein kinases by RT-PCR for the purposes of ultimately deducing their function, RNA was first isolated from a mouse mixed germ cell population. Degenerate primers targeting conserved regions in the subfamily of tyrosine kinases were employed and, following TA cloning, 27 sequences obtained as described in Methods were analyzed and compared with sequences in Gene Bank. Although most of the sequences match known members of the tyrosine kinase subfamily, some of the sequences obtained matched members of the subfamily of ser/thr protein kinases.

Between known members of this subfamily such as B-Rafkinase, a sequence with homology to a novel family of ser/thr protein kinases participating in spermiogenesis was detected (Kueng et al., 1997, *J Cell Biol* 139, 1851–9). To clone this novel ser/thr kinase, a 169 bases specific PCR fragment corresponding to this sequence was radiolabeled and a mouse mixed germ cell cDNA library was screened as described in Methods. A clone containing a 1.02 kb cDNA insert was obtained (SEQ ID NO: 10) and designated tssk-3b following the nomenclature of Kueng et al. Sequence analysis revealed a single open reading frame of 804 nucleotides encoding a 266 amino acids putative ser/thr protein kinase. The nucleotides flanking the start methionine conform well to Kozak consensus sequence. The 3'-untranslated region displays a polyadenylation signal 21 nucleotides upstream of the poly(A) tail. The sequence contains all the expected conserved domains corresponding to a ser/thr kinase.

Expression Pattern of Murine tssk3

The expression pattern of murine tssk-3b was investigated by northern blot analysis of total RNA from different mouse tissues using a tssk-3b specific probe corresponding to the full length transcript of tssk 3b. This probe recognized a single transcript of approximately 1 kb exclusively in the mixed mouse germ cell population prepared as described in Methods. At high exposures it is also possible to distinguish a 1.35 kb transcript also exclusively in germ cells, this transcript was not observed when the mouse germ cell library was screened and could represent a splicing alternative of tssk 3b. To further analyze the expression pattern of tssk-3b in the testis, a northern blot with RNA obtained from purified germ cells of the adult testis was probed. tssk-3b mRNA was found to be expressed postmeiotically in round and condensing spermatids but not in the meiotic pachytene spermatocytes. Mouse testes differentiate at d 11–12 of embryonic development and are populated by primordial germ cells. The first spermatogenic wave is initiated a few days after birth and spermatogonia differentiate to early spermatids before puberty. The differentiation to mature sperm is testosterone dependent and occurs after puberty.

To further investigate whether tssk-3b is expressed postmeiotically, total testis RNA was prepared from mice of different postnatal ages (1, 3, 7, 10, 15, 20, 24, 30 and adult) and analyzed by northern blot analysis. Transcription of tssk-3b began between 20 and 24 days after birth confirming a postmeiotic expression of this mRNA.

These results demonstrate that the expression pattern of tssk 3b is similar to that of mouse tssk 1 and tssk 2 (Kueng et al., 1997, *J Cell Biol* 139, 1851–9), suggesting that tssk 3 mRNA expression is developmentally regulated and that its expression is stimulated postmeiotically around the onset of spermiogenesis.

To further analyze the expression pattern of tssk 3b, we have performed RT-PCR using specific primers in oocytes, metaphase II-arrested eggs and different stages of preimplantation embryo development. No PCR product was observed at any of these stages under conditions in which the correct sized tssk 3b PCR product could be amplified from mixed germ cell total RNA.

Cloning and Expression of the Human Homologue of tssk 3b

Using the mouse tssk 3 sequence, a human EST from germ cell tumor was identified by a BLAST search of the databases, and used in conjunction with 3' and 5' RACE to clone the full length human homologue (SEQ ID NO: 3) from an adapted ligated human testis cDNA library (Clontech) as described in Methods.

To investigate the expression pattern of tssk 3 in human tissues, a tissue northern blot (Clontech) was probed with a C terminal 400 bp fragment of the human tssk3 cDNA. 1 kb and 1.35 kb RNA transcripts were expressed exclusively in the testis. Similar to the mouse case, the 1.35 kb fragment could represent an alternative spliced transcript. Both the mouse tssk 3b and the human homologue tssk 3 of these novel ser/thr kinases have the highest homology (98%) between each other, followed by mouse tssk3 (92%) mouse tssk1 and mouse tssk 2 (56%) suggesting that this kinase belongs to the same subfamily of novel ser/thr kinases. As mentioned, tssk 3 and tssk 3b have a very high homology (92%), the difference between these two sequences is restricted to a stretch of 22 aminoacids (residues 109 to 131). When this stretch is analyzed at the nucleotide level, three base pair deletions were observed in the mouse tssk 3 sequence that resulted in a shift in the coding region and an alteration of the aforementioned 22 amino acids. It is unclear at this moment the origin of these frame shifts, one possibility is that two different tssk 3 are present in mouse testis. More likely, one of these two sequences could have a small mistake in the sequence. Since the tssk 3 b human homologue was obtained independently from the mouse cDNA clone and has 100% homology at the amino acid level with its mouse homologue, applicants are confident about the accuracy of both the mouse 3b and the human tssk 3 sequences.

Chromosomal Mapping of Human and Murine tssk3.

The chromosomal location of tssk 3b has also been mapped by fluorescence in situ hybridization (FISH) using the full length human cDNA probe. Fluorescent signals were detected on chromosome 1 in all 20 metaphase spreads scored. Among a total of 109 signals observed, 49 (45%) were on 1 p. All chromosome-specific signals were localized to 1 p34.1–34.3. The distribution of signals was as follows: 1 chromatid (6 cells), two chromatids (14 cells) and three chromatids (5 cells). The mouse tssk 3b cDNA homologue mapped to the syntenic region in chromosome 4, band E.

EXAMPLE 2

Cloning of the Full Length cDNA of the Human Homologues of the tssk Kinase Family and a Partial cDNA Sequence from the tssk Substrate.

Using the predicted mouse tssk 1 and 2 amino acid sequences for the purposes of searching the gene bank, a genome sequence of both mouse tssk 1 and tssk2 was obtained. These genes mapped to chromosome 5 and 22 respectively and are intronless. The sequences corresponding to the 3' end and 5' end of the coding region were used to design sense and antisense primers respectively. The antisense primers were used in 5' RACE and the sense primer in 3' RACE using human testis marathon ready cDNA (Clontech, Inc.) as the template in order to ultimately obtain a full length sequence of both human kinase homologs. The amplified cDNA fragments were cloned using the TOPO TA cloning kit (Invitrogen) and sequenced. To amplify the full length human tssk kinases cDNA, the 5' end of the cDNA sequences obtained following 5' RACE were used to design a 5' sense primer. The 3' end of the cDNA sequences obtained following 3' RACE were used to design antisense primers. These two pairs of primers were then used to amplify human tssk1 and 2 from the same library. The amplified sequences 1.3 kb (tssk1) and of 1.2 kb (tssk 2) were subcloned and sequenced. The translated human homologues of the three members of the tssk kinase family are provided as SEQ ID NOS: 1–3, respectively.

To analyze the specificity of expression, commercial blots depicting several human tissues were performed using random primed-labeled probes from the full length cDNA of the human tssk 1 and 2. In addition a random prime-labeled probe from a partial 800 base pair sequence was used to determine the tissue distribution of the tssk substrate. Northern blots were performed using a commercially available human tissue blot (Clonetech).

Northern blots reveal that tssk 1, 2 and tssk substrate are testis specific mRNAs. These same blots were stripped to the tssk probes and reprobed with a beta actin sequence, confirming that each of the lanes was equally loaded with RNA. To further analyze the specificity of expression, the same probes were used to perform dot blots using commercially available mRNA arrays from 76 different human tissues (using the Multiple Tissue Expression (MTE™) Array from Clonetech, Cat # 7775-1. The only signal obtained in each of the probed MTEs is in the grid containing testis RNAS. This experiment confirmed that these messages are testis specific in human. In addition, Kueng et al. (1997) demonstrated that tssk 1 and 2 are postmeiotically expressed in mouse germ cells and that these messages are not present in other 11 tissues.

EXAMPLE 3

Immunolocalization and Immunoblotting Experiments

In order to determine if the tssk 1, 2 and 3 kinases and their substrate are present in the testis and/or mature sperm specific antibodies against the recombinant proteins will be generated. Alternatively, anti-peptide antibodies against specific peptides designed from the predicted amino acid sequence of each cDNA will be made. The specificity of each antibody generated will be tested against the recombinant tssk 1, 2 and 3. It is expected that the anti-peptide antibodies designed against specific amino acid sequences of each protein will be specific.

Antibodies made against tssk kinases and against the tssk substrate will be used to analyze for the presence of these kinases in other tissues. For this purpose, Clontech protein MedleysTM of different tissues such as brain, heart, kidney, liver, lung, ovary, placenta, skeletal muscle and spleen will be tested by western blot using the anti tssk and anti tssk substrate antibodies. Since mRNAs coding for tssk 1, 2 and 3 are only present in the testis, a similar protein distribution is expected. Since human homologues of tssk kinases have more than 80% homology when compared with their mouse counterparts, it is expected that antisera against the human recombinant tssk kinases recognize the mouse homologues as well. Thus, the antibodies made against the human tssk kinases will be also tested in mouse tissues.

To generate polyclonal antibodies against the purified recombinant protein. Rats and rabbits will be used for production of antibodies. Protocol as described by Mandal et al. (1999) will be followed for this purpose. Antibody titers will be monitored by ELISA and specificity of the antibody will be checked by SDS-PAGE and Western blotting analysis.

Sperm preparation.

In order to perform immunolocalization and immunoblotting experiments human sperm will be collected from healthy donors and purified using Percoll (Pharmacia Biotech, Upsala, Sweden) density gradient centrifugation as previously described (Naaby-Hansen et al., 1997). Sperm will be then resuspended to a final concentration of $2 \times 10^7$ cells/ml.

SDS-PAGE and Immunoblotting.

Sperm and other cell types from different tissues will be pelleted by centrifugation, washed in 1 ml of phosphate buffered saline (PBS), resuspended in sample buffer (Laemmli, 1970) without mercaptoethanol and boiled for 5 min. After centrifuging, the supernatant will be saved, 2-mercaptoethanol will be added to a final concentration of 5%, boiled for 5 min., and then subjected to 10% SDS-PAGE. Protein concentration will be determined by ABC kit from Pierce. Electrophoretic transfer of proteins to Immobilon P and immunodetection will be carried out as previously described (Kalab et al., 1994). Gels will be stained either with silver, coomasie blue or will be transferred to immobilon PVDF (Millipore) and probed with the anti recombinant antibodies.

Immunofluorescence.

To determine the intracellular location of tssk 1, 2 and 3, the specific antibodies against the soluble enzyme will be used in immunofluorescence experiments and immunoelectromicroscopy of human testicular tissue and human sperm. In addition, if the antibodies recognize the mouse antigens, the localization will be explored by immunofluorescence in mouse germ cells and sperm.

Sperm will be treated in the appropriate experimental conditions, fixed in suspension with a solution of 3% (w/v) paraformaldehyde-0.05% (v/v) glutaraldehyde in PBS for 1 h, washed in PBS at 37 C, and then permeabilized with 0.1% (v/v) Triton X-100 in PBS at 37 C for 10 min. The sperm will then be washed in PBS and incubated overnight with serial dilutions (5, 10, 50 and 100) of the appropriate antibody as previously described (Visconti et al., 1996). After washing the sperm with PBS, they will be incubated with FITC-coupled goat anti mouse IgG and then attached to poly-lysine-coated microscope slides. Following 3× washes with PBS, the slides will be mounted with fluoromont and fluorescence will be assessed. Testicular samples obtained from testicular biopsies will be processed as previosly described (Westbrook et al., 2000).

EXAMPLE 4

Expression of Recombinant tssk Protein

Since many kinases have been expressed as active molecule in *E. coli* (Bodenbach et al., 1994; Letwin et al., 1992). Advantage will be taken of *E coli's* relatively simple, easy-to scale-up. Open reading frames of TSSK1, 2, 3 will be amplified and fused with his tag in pET28b vector (Novagen). The plasmid will be transformed into BL21 DE3 or other appropriate host strain. Recombinant protein production will be induced by addition of IPTG to 1 mM final in the cultural medium. Recombinant protein will be purified from *E coli* lysate using Ni-NTA column under native condition. To facilitate crystal formation, highly purified protein is optimal. To purify the protein preparation from above, preparative electrophoresis using PrepCell (BIO-RAD) will be employed. Kinase assay will be conducted before proceeding to crystallography.

To produce recombinant testicular tssk kinases and tssk substrate in bacteria, expression constructs of tssk 1, 2 and 3 as well as for the tssk substrate will be made. The coding region of each of these proteins will be subcloned in the pET28b expression vector that contains at the C-terminus 6 residues of His-tag. In particular, the constructs will be made using complete ORF. primers that are designed to create an NdeI site at the 5' end and an XhoI site at the 3' end. The amplified products will be ligated into the NdeI-XhoI sites of pET28b expression vector. Since the recombinant protein will be fused with the 6 histidine residues of the expression vector the expressed protein will be purified using Ni-Histidine bind resin affinity chromatography. Once purified, kinase activity will be evaluated with the tssk substrate to make sure that the enzyme has folded correctly.

TSSK 2 protein was successfully expressed in *E. coli* and purified. To express tssk 2, the open reading frame was subcloned into a pET28b expression vector carrying a His-tag. Recombinant protein was produced following induction with IPTG. Bacterially expressed and partially purified tssk2 was further purified by preparative gel electrophoresis using a PrepCell from Biorad. The fractions were collected and analyzed by SDS-PAGE. TSSK substrate was expressed and purified similarly. These purified proteins were used to produce rat polyclonal antibodies using standard techniques.

Since multiple kinases have the property to become autophosphorylated in vivo and in vitro, purified bacterially expressed recombinant tssk 2 was assayed for autophosphorylation. The experiment was conducted in the presence of 40 µM ATP (1 µCi of [$^{32}$P] ATP), 10 mM $Mg^{2+}$, phosphatases inhibitors such as p-nitro-phenyl phosphate and glycerol phosphate and proteases inhibitors (leupeptin and aprotinin 10 µg/ml), the assay was stopped with sample buffer and tssk 2 was separated in 10% PAGE. Auto radiography of the dried gel showed that recombinant tssk 2 incorporated $^{32}$P, suggesting that the bacterially expressed tssk 2 folded correctly for phosphorylation to occur and could be used for structural studies Since not all bacterial expressed recombinant proteins are folded correctly, a similar approach will be taken to express tssk 1, 2 and 3 in yeasts. In order to express the tssk kinases and substrate in yeasts, the kinases will be subcloned in pPICZαB vector from Invitrogen (Carlsbad, Calif.) and will be expressed in *Pichia pastoris* as secreted protein as well as an intracellular protein. These constructs also have a C-terminal His tag that will allow an easy purification of the recombinant proteins either from the culture media or from the extracted cells.

EXAMPLE 5

Tssk 2 Interacts with tsks in a Yeast Two-Hybrid System

To demonstrate protein-protein interaction between tssk 2 and tsks a two yeast hybrid system was utilized. In this experiment, a bait gene (tssk 2) was first transformed into the reporter strain as a fusion to the GAL4 DNA binding domain (DNA-BD). A second plasmid that expressed tsks as fusion to the GAL 4 activation domain (AD) was also introduced into the AH109 reporter strain. Western blots were performed to confirm expression of fusion proteins in yeast. Interaction between tssk 2 and tsks was observed to promote transcription of the Histidine (HIS) gene and allow for the growth of yeast in His-free medium. Similarly, cotransfection of yeast cells with a first construct expressing a p53 fused to the GAL4 DNA binding domain and a second construct expressing the SV40 Large T antigen fused to the GAL 4 activation domain (AD) demonstrated that p53 and the SV40 Large T antigen interacted and promoted His gene activation. This interaction was used as a positive control. In contrast, fusion proteins of TSSK2 and p53 with the DNA-BD did not promote growing when cotransfected with the GAL-AD plasmid. Neither GAL-AD alone nor the fusion proteins between GAL-AD and TSKS or GAL-AD and SV40 Large T antigen had the ability to activate transcription of the His gene. This experiment demonstrated that tssk 2 and the substrate tsks are able to interact, suggesting that the human homologues of these proteins behave in a similar way to their mouse counterparts.

To investigate whether tssk 2 and tsks also interact in vivo, capacitated and non capacitated sperm will be extracted with Triton X 100 in conditions that protect protein-protein interaction and then immunoprecipitation will be conducted with specific antibodies. The interaction will be assayed by Western blots with the other antibody in a typical cross immunoprecipitation experiment. Since proteins that interact should co-localized, double labeling immunofluorescence will be conducted and co-localization investigated. Although rabbit antibodies have not yet been obtained for the human tssks, rat anti tssk 2 and rat anti tsks antibodies have been previously obtained and therefore there is no reason to anticipate any difficulties in obtaining antibodies to the human tssks.

EXAMPLE 6

Isolation of the Crystal Structure of tssk 1, 2, 3 and the tssk Substrate

Two strategies will be followed for the rationale design of tssk-specific inhibitors. First, an in vitro kinase assay compatible with High Throughput screening will be developed. Second, crystal structure of tssk kinases alone or complexed with their substrate will be obtained.

For structural studies using X-ray crystallography, it is necessary to obtain approximately 5 mg of the active kinases. This amount of protein is generally a suitable quantity for initial crystallization trials. Initial trials will be performed on the recombinant intact protein; this is a common crystallization technique that has proven to be successful in many cases, including several structural studies of enzymes. Prior to crystallization screening, the expressed fragment would be checked for a suitable level of enzymatic activity as well as for purity, homogeneity and solubility. Several commercially available crystallization screening kits, used in conjunction with the hanging drop vapor diffusion method, provide the standard first step in the search for crystal growth conditions. Crystallization screening of the fragment in the presence of catalytically required metal ions, substrates and/or inhibitors will be carried out simultaneously with the screen of the apoenzyme.

Crystals will be obtained at 21° C. by equilibrating sitting drops. For cryodiffraction experiments, the crystals will be transferred to a similarly buffered solution through three solutions with intermediate concentrations of these reagents. For diffraction experiments at room temperature and lower resolution, Cu Kα radiation from rotating anode X-ray generators will be used. Final structure will be established after preliminary refinement, model improvement and further improvement.

In the case of the tssk kinase family, crystallization in the presence of their substrate will be attempted in order to establish a molecular basis of the kinase activity. Once initial crystallization conditions are obtained, they will be optimized in order to obtain crystals that diffract to at least 3.0 Å resolution. Direct phasing of the structure via the MAD (multiple wavelength anomalous dispersion) and MIR (multiple isomorphous replacement) techniques would be carried out simultaneously, to assure success. Semi-automated model-building and refinement techniques for phased structures would be utilized to achieve rapid structural results. Once a structure is obtained, the results will be analyzed with a view to understanding the unique role of the tssk kinase family in spermatogenesis and/or sperm function. An ultimate goal of these studies would be the use of the structure as a template for the design of specific inhibitors of tssk 1, 2 and/or 3, which may prove useful as contraceptives.

EXAMPLE 7

Development of a tssk-Specific Kinase Assay.

The design of a specific kinase assay for the tssk family is advantageous from different points of view. First, an kinase assay will allow for the characterization of the kinetic properties of these enzymes such as the Km for ATP, divalent cation and substrate. Second, since only active enzymes are suitable for crystallographic studies, a kinase assay will confirm the folding of the recombinant proteins. Third, it is desireable to develop an in vitro kinase assay at the lab scale to be the basis to a kinase assay appropriate for high throughput screening of tssk-specific inhibitors.

Development of assays to measure tssk kinase activity will follow general characteristics of kinase assays such as presence of substrate, [γ32P]ATP, $Mg^{2+}$ and/or $Mn^{2+}$ and phosphatases inhibitors. First however a source of tssk kinase must be provided. The tssk kinase will be generated by recombinantly expressing these proteins and purifying the expressed kinase.

Kinase Assay in Mammalian Cell Extracts.

ORFs of the respective human tssk kinases will be subcloned in a pCMV-HA epitope-tagged mammalian expression vector (Clontech cat # K6003-1). Similarly, the ORF of the tssk substrate will be subcloned in a pCMV-Myc mammalian expression vector (Clontech, same as above). Each of the three HA-kinases will be coexpressed with the cMyc-tssk substrate in three separate COS cell lines for each of the respective human tssks. Coexpression will be validated performing immunofluorescence with the respective antitag antibodies. Antibodies against HA and Myc are available from Clontech. Since anti c-Myc is a mouse monoclonal and anti HA is a rabbit polyclonal, it will be possible to analyze whether both the kinase and the substrate were coexpressed in the same cells.

Proteins will be then extracted with 1% Triton and immunoprecipitation will be performed using anti HA-tag antibodies. Alternatively, anti tssk-kinase/anti-tssk substrate antibodies could be used to immunoprecipitate the tssk kinases and tssk substrate. Typically the antibodies will be linked to a solid support such as a sepharose bead to assist in the isolation of the target ligand. After precipitation with Protein A sepharose, the pellet will be assayed for kinase activity using different concentrations of ATP (10 μM, 100 μM and 1 mM), $Mg^{2+}$ or $Mn^{2+}$ (100 μM, 1 mM and 10 mM) and 1 μCi of [γ32P] ATP. The phosphorylated protein will be evaluated following SDS-PAGE separation and autoradiography. The evaluation of kinase activity after immunoprecipitation is a frequently used method that allow for specific measurement of the activity of one particular kinase (Coso et al., 1995, *Cell* 81, 1137–46; Moos et al., 1995, *Biol Reprod* 53, 692–9). Since Kueng et al. (1997) has successfully detected the phosphorylation of tssk substrate after immunoprecipitation of tssk 1 and 2, it is expected that it will be possible to measure kinase activity of tssk kinases after coexpression in a mammalian system.

In Vitro Kinase Assay.

Each purified enzyme will be mixed with different concentrations of ATP (10 μM, 100 μM and 1 mM), $Mg^{2+}$ or $Mn^{2+}$ (100 μM, 1 mM and 10 mM), 1 μCi of [γ32P] ATP and different concentrations of the purified tssk substrate (1, 10 and 100 ng/assay). Phosphorylation will be evaluated following SDS-PAGE separation and autoradiography. It is expected that if the proteins are correctly folded the phosphorylation of the substrate will be easily detected with this methodology.

EXAMPLE 8

Generation of tssk Antibodies

Purified tssk 2 and tsks were used to produce rat polyclonal antibodies. Antisera against recombinant human tssk 1, 2 and 3 as well as to the human tssk substrate will be employed to define their tissue distribution and subcellular localization at the protein level. The rat anti-tssk and anti-tsks antibodies recognized the recombinant protein and also proteins in sperm and testes with the predicted MW, suggesting that at least one member of the tssk family and their substrate (tsks) are present in sperm. These antibodies were then used to study the intracellular localization of these proteins in capacitated human sperm. Tssk 2 was observed to localized to the equatorial segment of human sperm. Tsks also localized to the equatorial segment. Nevertheless antitsks antibody also recognize proteins present in the anterior head and in the tail. Immunolocalization of these molecules suggests that tssk 2 and tsks are present in similar region of the sperm at least in a fraction of the human sperm population. Control experiments were performed using rat pre immune serum of the respective antibody. Both Western blots and immunofluorescence were negative. Although the antibody against tssk 2 was produced against tssk 2, we can not discard that this antibody recognized other members of the tssk family since their sequences have high homology. However, discrimination between the three tssk isoenzymes, may be possible by generating antibodies against the C-terminal domain that is different between tssk 1 and 2 and is not present in tssk 3.

The invention claimed is:

1. A method of screening for potential human therapeutic agents, said method comprising contacting a tssk polypeptide comprising SEQ ID NO: 6 with a candidate compound in the presence of a tssk substrate set forth as SEQ ID NO:8; and determining if the candidate compound selectively binds to said polypeptide by measuring a change in the rate of SEQ ID NO:8 phosphorylation relative to that observed in the assays conducted in the absence of said candidate compound.

2. The method of claim 1 wherein the tssk polypeptide is immobilized on a solid surface and the candidate compound is labeled.

3. A method for identifying antagonists of tssk activity wherein said tssk comprises SEQ ID NO:6, said method comprising providing an in vitro kinase assay composition, said composition comprising a labeled source of phosphate, a tssk substrate set forth as SEQ ID NO:8 and a tssk, wherein said tssk comprises SEQ ID NO: 6;

measuring the rate of phosphorylation of said substrate in the presence and absence of a candidate inhibitory compound; and identifying antagonist compounds that decrease the tssk kinase activity relative to the kinase activity observed in the assays conducted in the absence of the antagonist compound.

4. The method of claim 3 wherein the labeled source of phosphate is ATP.

* * * * *

SEQUENCE LISTING

<160> NUMBER OF SEQ ID NOS: 18

<210> SEQ ID NO 1
<211> LENGTH: 1352
<212> TYPE: DNA
<213> ORGANISM: Homo sapiens

<400> SEQUENCE: 1

```
tctatccagg atgtaaatga gcacactgct ggcccatgcg cctcggggct gtagagggca      60
gcctcagagg cactgggcat tcctggcacc atggatgacc tgctgtcct caagcgacga     120
ggctacctcc tggggataaa tttaggagag ggctcctatg caaaagtaaa atctgcttac    180
tctgagcgcc tgaagttcaa tgtggcgatc aagatcatcg accgcaagaa ggcccccgca    240
gacttcttgg agaaattcct tccccgggaa attgagattc tggccatgtt aaaccactgc    300
tccatcatta agacctacga gatctttgag acatcacatg gcaaggtcta catcgtcatg    360
gagctcgcgg tccagggcga cctcctcgag ttaatcaaaa cccggggagc cctgcatgag    420
gacgaagctc gcaagaagtt ccaccagctt tccttggcca tcaagtactg ccacgacctg    480
gacgtcgtcc accgggacct caagtgtgac aaccttctcc ttgacaagga cttcaacatc    540
aagctgtccg acttcagctt ctccaagcgc gtcctgcggg atgacagtgg tcgaatggca    600
ttaagcaaga ccttctgtgg gtcaccagcg tatgcggccc cagaggtgct gcagggcatt    660
ccctaccagc ccaaggtgta cgacatctgg agcctaggcg tgatcctcta catcatggtc    720
tgcggctcca tgcctacga cgactccaac atcaagaaga tgctgcgtat ccagaaggag    780
caccgcgtca acttcccacg ctccaagcac ctgacaggcg agtgcaagga cctcatctac    840
cacatgctgc agcccgacgt caaccggcgg ctccacatcg acgagatcct cagccactgc    900
tggatgcagc ccaaggcacg gggatctccc tctgtggcca tcaacaagga ggggagagt    960
tcccggggaa ctgaacccttt gtggacccccc gaacctggct ctgacaagaa gtctgccacc   1020
aagctggagc tgagggaga ggcacagccc caggcacagc ctgagacaaa acccgagggg   1080
acagcaatgc aaatgtccag gcagtcggag atcctgggtt tccccagcaa gccgtcgact   1140
atggagacag aggaagggcc cccccaacag cctccagaga cgcgggccca gtgagcttct   1200
tgcggcccag ggaatgagat ggagctcacg gcttaaagcc caagctctga agaagtcaag   1260
ggtggagcca gagaaggaag gcagtcccag atgagcctct attttcatca gcttcttctc   1320
tctccccttg aacttggtaa cccacatggt tc                                 1352
```

<210> SEQ ID NO 2
<211> LENGTH: 1254
<212> TYPE: DNA
<213> ORGANISM: Homo sapiens

<400> SEQUENCE: 2

```
ttgaggacaa cgcctgctgg cccacatgac ggggggatgt agacggcagc ggcgccagtc      60
gctcctggca ccatggacga tgccacagtc ctaaggaaga agggttacat cgtaggcatc     120
aatcttggca agggttccta cgcaaaagtc aaatctgcct actctgagcg cctcaagttc     180
aatgtggctg tcaagatcat cgaccgcaag aaaacaccta ctgactttgt ggagagattc     240
cttcctcggg agatggacat cctggcaact gtcaaccacg gctccatcat caagacttac     300
gagatctttg agacctctga cggacggatc tacatcatca tggagcttgg cgtccagggc     360
gacctcctcg agttcatcaa gtgccaggga gccctgcatg aggacgtggc acgcaagatg     420
```

-continued

```
ttccgacagc tctcctccgc cgtcaagtac tgccacgacc tggacatcgt ccaccgggac      480
ctcaagtgcg agaaccttct cctcgacaag gacttcaaca tcaagctgtc tgactttggc      540
ttctccaagc gctgcctgcg ggacagcaat gggcgcatca tcctcagcaa gaccttctgc      600
gggtcggcag catatgcagc ccccgaggtg ctgcagagca tcccctacca gcccaaggtg      660
tatgacatct ggagcctggg cgtgatcctg tacatcatgg tctgcggctc catgccctat      720
gacgactccg acatcaggaa gatgctgcgt atccagaagg agcaccgtgt ggacttcccg      780
cgctccaaga acctgacctg cgagtgcaag gacctcatct accgcatgct gcagcccgac      840
gtcagccagc ggctccacat cgatgagatc ctcagccact cgtggctgca gccccccaag      900
cccaagccaa cgtcttctgc ttccttcaag agggaggggg agggcaagta ccgcgctgag      960
tgcaaactgg acaccaagac aggcttgagg cccgaccacc ggcccgacca caagcttgga     1020
gccaaaaccc agcaccggct gctggtggtg cccgagaacg agaacaggat ggaggacagg     1080
ctggccgaga cctccagggc caaagaccat cacatctccg gagctgaggt ggggaaagca     1140
agcacctagc atgacaatgg ccccgttgtg tgtggtgggg gtcggggttg gggggcatgg     1200
tgcagtcggc cttcacgtaa actaagtagg caggtaggat ctgaagaagg caca           1254
```

<210> SEQ ID NO 3
<211> LENGTH: 1058
<212> TYPE: DNA
<213> ORGANISM: Homo sapiens

<400> SEQUENCE: 3

```
catcctaata cgactcacta tagggctcga gcggcgcccg ggcaggtgag aatgttctaa       60
cgctgggggc ggctgcggat gaagtccttg gggagaaaag gagcaggcca agggcgatgg      120
tggagtagag ctgcctctca gaggcagcat gagctgagag ggtgatagga aggcggcgct      180
agacagcatg gaggactttc tgctctccaa tgggtaccag ctgggcaaga ccattgggga      240
agggacctac tcaaaagtca agaagcattt tccaaaaaaa caccaaagaa agtggcaat       300 taaagttata gacaagatgg gagggccaga agagtttatc cagagattcc tccctcggga      360
gctccaaatc gtccgtaccc tggaccacaa gaacatcatc caggtgtatg agatgctgga      420
gtctgccgac gggaaaatct gcctggtgat ggagctcgct gagggagggg atgtcttga      480 ctgcgtgctg aatgggggc cactgcctga agccgggcc aaggccctct tccgtcagat       540
ggttgaggcc atccgctact gccatggctg tggtgtggcc caccgggacc tcaaatgtga      600
gaacgccttg ttgcagggct tcaacctgaa gctgactgac tttggctttg ccaaggtgtt      660
gcccaagtca caccgggagc tgagccagac cttctgcggc agtacagcct atgctgcccc      720
cgaggtgctg caggcattcc cccacgatag caaaaaggt gatgtctgga gcatgggtgt      780
ggtcctgtat gtcatgctct gtgccagcct accttttgac gacacagaca tcccaagat       840 gctgtggcag cagcagaagg gggtgtcctt ccccactcat ctgagcatct cggccgattg      900
ccaggacctg ctcaagaggc tcctggaacc cgatatgatc ctccggcctt caattgaaga      960
agttagttgg catccatggc tagcaagcac ttgataaaag caatgcaag tgctctccaa      1020 taaagtaggg ggagaaagca agcaaaccc aaaaaaaa                              1058
```

<210> SEQ ID NO 4
<211> LENGTH: 367
<212> TYPE: PRT
<213> ORGANISM: Homo sapiens

<400> SEQUENCE: 4

```
Met Asp Asp Ala Ala Val Leu Lys Arg Arg Gly Tyr Leu Leu Gly Ile
1               5                  10                  15

Asn Leu Gly Glu Gly Ser Tyr Ala Lys Val Lys Ser Ala Tyr Ser Glu
            20                  25                  30

Arg Leu Lys Phe Asn Val Ala Ile Lys Ile Ile Asp Arg Lys Lys Ala
        35                  40                  45

Pro Ala Asp Phe Leu Glu Lys Phe Leu Pro Arg Glu Ile Glu Ile Leu
    50                  55                  60

Ala Met Leu Asn His Cys Ser Ile Ile Lys Thr Tyr Glu Ile Phe Glu
65                  70                  75                  80

Thr Ser His Gly Lys Val Tyr Ile Val Met Glu Leu Ala Val Gln Gly
                85                  90                  95

Asp Leu Leu Glu Leu Ile Lys Thr Arg Gly Ala Leu His Glu Asp Glu
            100                 105                 110

Ala Arg Lys Lys Phe His Gln Leu Ser Leu Ala Ile Lys Tyr Cys His
        115                 120                 125

Asp Leu Asp Val Val His Arg Asp Leu Lys Cys Asp Asn Leu Leu Leu
145 130                 135                 140

Asp Lys Asp Phe Asn Ile Lys Leu Ser Asp Phe Ser Phe Ser Lys Arg
145                 150                 155                 160

Cys Leu Arg Asp Asp Ser Gly Arg Met Ala Leu Ser Lys Thr Phe Cys
                165                 170                 175

Gly Ser Pro Ala Tyr Ala Ala Pro Glu Val Leu Gln Gly Ile Pro Tyr
            180                 185                 190

Gln Pro Lys Val Tyr Asp Ile Trp Ser Leu Gly Val Ile Leu Tyr Ile
        195                 200                 205

Met Val Cys Gly Ser Met Pro Tyr Asp Asp Ser Asn Ile Lys Lys Met
210                 215                 220

Leu Arg Ile Gln Lys Glu His Arg Val Asn Phe Pro Arg Ser Lys His
225                 230                 235                 240

Leu Thr Gly Glu Cys Lys Asp Leu Ile Tyr His Met Leu Gln Pro Asp
                245                 250                 255

Val Asn Arg Arg Leu His Ile Asp Glu Ile Leu Ser His Cys Trp Met
            260                 265                 270

Gln Pro Lys Ala Arg Gly Ser Pro Ser Val Ala Ile Asn Lys Glu Gly
        275                 280                 285

Glu Ser Ser Arg Gly Thr Glu Pro Leu Trp Thr Pro Glu Pro Gly Ser
290                 295                 300

Asp Lys Lys Ser Ala Thr Lys Leu Glu Pro Glu Gly Glu Ala Gln Pro
305                 310                 315                 320

Gln Ala Gln Pro Glu Thr Lys Pro Glu Gly Thr Ala Met Gln Met Ser
                325                 330                 335

Arg Gln Ser Glu Ile Leu Gly Phe Pro Ser Lys Pro Ser Thr Met Glu
            340                 345                 350

Thr Glu Glu Gly Pro Pro Gln Gln Pro Pro Glu Thr Arg Ala Gln
        355                 360                 365
```

<210> SEQ ID NO 5
<211> LENGTH: 358
<212> TYPE: PRT
<213> ORGANISM: Homo sapiens

<400> SEQUENCE: 5

```
Met Asp Asp Ala Thr Val Leu Arg Lys Lys Gly Tyr Ile Val Gly Ile
1               5                   10                  15

Asn Leu Gly Lys Gly Ser Tyr Ala Lys Val Lys Ser Ala Tyr Ser Glu
            20                  25                  30

Arg Leu Lys Phe Asn Val Ala Val Lys Ile Ile Asp Arg Lys Lys Thr
        35                  40                  45

Pro Thr Asp Phe Val Glu Arg Phe Leu Pro Arg Glu Met Asp Ile Leu
    50                  55                  60

Ala Thr Val Asn His Gly Ser Ile Ile Lys Thr Tyr Glu Ile Phe Glu
65                  70                  75                  80

Thr Ser Asp Gly Arg Ile Tyr Ile Ile Met Glu Leu Gly Val Gln Gly
                85                  90                  95

Asp Leu Leu Glu Phe Ile Lys Cys Gln Gly Ala Leu His Glu Asp Val
            100                 105                 110

Ala Arg Lys Met Phe Arg Gln Leu Ser Ser Ala Val Lys Tyr Cys His
        115                 120                 125

Asp Leu Asp Ile Val His Arg Asp Leu Lys Cys Glu Asn Leu Leu Leu
    130                 135                 140

Asp Lys Asp Phe Asn Ile Lys Leu Ser Asp Phe Gly Phe Ser Lys Arg
145                 150                 155                 160

Cys Leu Arg Asp Ser Asn Gly Arg Ile Ile Leu Ser Lys Thr Phe Cys
                165                 170                 175

Gly Ser Ala Ala Tyr Ala Ala Pro Glu Val Leu Gln Ser Ile Pro Tyr
            180                 185                 190

Gln Pro Lys Val Tyr Asp Ile Trp Ser Leu Gly Val Ile Leu Tyr Ile
        195                 200                 205

Met Val Cys Gly Ser Met Pro Tyr Asp Asp Ser Asp Ile Arg Lys Met
    210                 215                 220

Leu Arg Ile Gln Lys Glu His Arg Val Asp Phe Pro Arg Ser Lys Asn
225                 230                 235                 240

Leu Thr Cys Glu Cys Lys Asp Leu Ile Tyr Arg Met Leu Gln Pro Asp
                245                 250                 255

Val Ser Gln Arg Leu His Ile Asp Glu Ile Leu Ser His Ser Trp Leu
            260                 265                 270

Gln Pro Pro Lys Pro Lys Ala Thr Ser Ser Ala Ser Phe Lys Arg Glu
        275                 280                 285

Gly Glu Gly Lys Tyr Arg Ala Glu Cys Lys Leu Asp Thr Lys Thr Gly
    290                 295                 300

Leu Arg Pro Asp His Arg Pro Asp His Lys Leu Gly Ala Lys Thr Gln
305                 310                 315                 320

His Arg Leu Leu Val Pro Glu Asn Glu Asn Arg Met Glu Asp Arg
                325                 330                 335

Leu Ala Glu Thr Ser Arg Ala Lys Asp His His Ile Ser Gly Ala Glu
            340                 345                 350

Val Gly Lys Ala Ser Thr
        355

<210> SEQ ID NO 6
<211> LENGTH: 268
<212> TYPE: PRT
<213> ORGANISM: Homo sapiens

<400> SEQUENCE: 6

Met Glu Asp Phe Leu Leu Ser Asn Gly Tyr Gln Leu Gly Lys Thr Ile
1               5                   10                  15
```

Gly Glu Gly Thr Tyr Ser Lys Val Lys Glu Ala Phe Ser Lys Lys His
         20                  25                  30

Gln Arg Lys Val Ala Ile Lys Val Ile Asp Lys Met Gly Gly Pro Glu
         35                  40                  45

Glu Phe Ile Gln Arg Phe Leu Pro Arg Glu Leu Gln Ile Val Arg Thr
         50                  55                  60

Leu Asp His Lys Asn Ile Ile Gln Val Tyr Glu Met Leu Glu Ser Ala
65                  70                  75                  80

Asp Gly Lys Ile Cys Leu Val Met Glu Leu Ala Glu Gly Gly Asp Val
                 85                  90                  95

Phe Asp Cys Val Leu Asn Gly Gly Pro Leu Pro Glu Ser Arg Ala Lys
                100                 105                 110

Ala Leu Phe Arg Gln Met Val Glu Ala Ile Arg Tyr Cys His Gly Cys
             115                 120                 125

Gly Val Ala His Arg Asp Leu Lys Cys Glu Asn Ala Leu Leu Gln Gly
         130                 135                 140

Phe Asn Leu Lys Leu Thr Asp Phe Gly Phe Ala Lys Val Leu Pro Lys
145                 150                 155                 160

Ser His Arg Glu Leu Ser Gln Thr Phe Cys Gly Ser Thr Ala Tyr Ala
                 165                 170                 175

Ala Pro Glu Val Leu Gln Gly Ile Pro His Asp Ser Lys Lys Gly Asp
             180                 185                 190

Val Trp Ser Met Gly Val Val Leu Tyr Val Met Leu Cys Ala Ser Leu
         195                 200                 205

Pro Phe Asp Asp Thr Asp Ile Pro Lys Met Leu Trp Gln Gln Gln Lys
210                 215                 220

Gly Val Ser Phe Pro Thr His Leu Ser Ile Ser Ala Asp Cys Gln Asp
225                 230                 235                 240

Leu Leu Lys Arg Leu Leu Glu Pro Asp Met Ile Leu Arg Pro Ser Ile
                245                 250                 255

Glu Glu Val Ser Trp His Pro Trp Leu Ala Ser Thr
             260                 265

SEQ ID NO 7
LENGTH: 1779
TYPE: DNA
ORGANISM: Homo sapiens

SEQUENCE: 7 atggcgagcg tggtggtgaa gacgatctgg cagtccaaag agatccatga ggccggggac    60
accccacggg gggtggagag ctgctcccag ctagtcccag aggctccccg gagggtgacc   120
agccgggcca agggatcccc gaagaaaaag aaggccgtgt cgttccacgg ggtggagccc   180
cagatgtccc atcagcccat gcactggtgc ctgaacctca acggtcctc ggcctgcacc    240 aacgtgtcac tgctcaacct ggccgccatg agcccactg actccacggg gacagactcc    300
acagtggaag acctcagcgg ccaactcaca ctggctgggc cccctgcctc ccctacccta   360
ccctgggatc cggatgacgc agacatcacg gaaatcctga gtggggtcaa cagtggattg   420
gtccgcgcca agactccat caccagcttg aaggaaaaga ccaaccgggt taaccagcac    480
gtgcagtctc tgcagagcga gtgttctgtg ctgagcgaga atctggaggg aaggcggcaa   540
gaggcagaag agttggaggg gtactgcatt caactcaagg agaactgctg gaaggtgacc   600
cggtctgtgg aagatgctga aatcaaaacc aacgtcttga gcagaattc tgccctgctg   660

-continued

```
gaggagaagt tgcgctacct ccagcagcag ctgcaggatg agacgccgcg acggcaggag    720
gccgagctgc aggagccgga ggagaagcag gagccggagg agaagcagga gccggaggag    780
aagcagaagc cggaggctgg cctctcctgg aacagcctgg ccccgccgc cacgtcccag     840 ggctgccccg gcccgccagg gagtcccgac aaaccctcgc ggccacacgg cctggtcccc    900
gcaggctggg gaatgggggcc tcgggctggc gagggcccct acgtgagcga gcaggaattg    960
cagaagctgt tcaccggcat cgaagagctg aggagagagg tgtcctcact gaccgcccgg   1020
tggcatcagg aggaggggc ggtgcaggaa gccctgcggc tgctcggggg cctgggcggc    1080
agggtcgacg gcttcctagg ccagtgggag cgggcacagc gcgaacaggc acagacggcg   1140
cggggcttgc aggagctgcg aggtcgggcg gatgagctgt gcaccatggt ggagcggtca   1200
gcagtgtctg tggcttcact gaggagcgaa ctggaggggc tgggcccact gaaacccatt   1260
ctggaggagt tcgggcggca atttcagaac tctcgaagag gcctgacct ctccatgaac    1320 ctggatcggt cccaccaagg caactgtgcc cgctgtgcca gccaggggtc gcagttgtct   1380
acggagtccc tgcagcagct gctggaccga gcactgacct cactagtgga cgaggtgaag   1440
cagaggggcc tgactcctgc ctgtcccagc tgtcagaggc tacacaagaa gattctggag   1500
ctggagcgcc aggccttagc caaacacgtc agggcagagg ccctgagctc cacccttcgg   1560
ctggcccaag cgaggccct gcgggccaag aacctactgc tgacagacaa gatgaagcca    1620
gaggagaaga tggccactct ggaccatcta cacttgaaga tgtgctccct ccacgatcat   1680
ctcagcaacc tgccacttga ggggtccacg ggaacaatgg ggggaggcag cagtgcagga   1740 accccccccaa aacagggggg ctcagccccT gaacaataa                         1779
```

<210> SEQ ID NO 8
<211> LENGTH: 592
<212> TYPE: PRT
<213> ORGANISM: Homo sapiens

<400> SEQUENCE: 8

```
Met Ala Ser Val Val Lys Thr Ile Trp Gln Ser Lys Glu Ile His
1               5                  10                  15

Glu Ala Gly Asp Thr Pro Thr Gly Val Glu Ser Cys Ser Gln Leu Val
            20                  25                  30

Pro Glu Ala Pro Arg Arg Val Thr Ser Arg Ala Lys Gly Ile Pro Lys
        35                  40                  45

Lys Lys Lys Ala Val Ser Phe His Gly Val Glu Pro Gln Met Ser His
    50                  55                  60

Gln Pro Met His Trp Cys Leu Asn Leu Lys Arg Ser Ser Ala Cys Thr
65                  70                  75                  80

Asn Val Ser Leu Leu Asn Leu Ala Ala Met Glu Pro Thr Asp Ser Thr
                85                  90                  95

Gly Thr Asp Ser Thr Val Glu Asp Leu Ser Gly Gln Leu Thr Leu Ala
            100                 105                 110

Gly Pro Pro Ala Ser Pro Thr Leu Pro Trp Asp Pro Asp Ala Asp
        115                 120                 125

Ile Thr Glu Ile Leu Ser Gly Val Asn Ser Gly Leu Val Arg Ala Lys
    130                 135                 140

Asp Ser Ile Thr Ser Leu Lys Glu Lys Thr Asn Arg Val Asn Gln His
145                 150                 155                 160

Val Gln Ser Leu Gln Ser Glu Cys Ser Val Leu Ser Glu Asn Leu Glu
                165                 170                 175
```

-continued

```
Gly Arg Arg Gln Glu Ala Glu Leu Glu Gly Tyr Cys Ile Gln Leu
            180                 185                 190

Lys Glu Asn Cys Trp Lys Val Thr Arg Ser Val Glu Asp Ala Glu Ile
        195                 200                 205

Lys Thr Asn Val Leu Lys Gln Asn Ser Ala Leu Leu Glu Glu Lys Leu
    210                 215                 220

Arg Tyr Leu Gln Gln Gln Leu Gln Asp Glu Thr Pro Arg Arg Gln Glu
225                 230                 235                 240

Ala Glu Leu Gln Glu Pro Glu Lys Gln Glu Pro Glu Glu Lys Gln
                245                 250                 255

Glu Pro Glu Glu Lys Gln Lys Pro Glu Ala Gly Leu Ser Trp Asn Ser
            260                 265                 270

Leu Gly Pro Ala Ala Thr Ser Gln Gly Cys Pro Gly Pro Pro Gly Ser
        275                 280                 285

Pro Asp Lys Pro Ser Arg Pro His Gly Leu Val Pro Ala Gly Trp Gly
    290                 295                 300

Met Gly Pro Arg Ala Gly Glu Gly Pro Tyr Val Ser Glu Gln Glu Leu
305                 310                 315                 320

Gln Lys Leu Phe Thr Gly Ile Glu Glu Leu Arg Arg Glu Val Ser Ser
                325                 330                 335

Leu Thr Ala Arg Trp His Gln Glu Gly Ala Val Gln Glu Ala Leu
            340                 345                 350

Arg Leu Leu Gly Gly Leu Gly Gly Arg Val Asp Gly Phe Leu Gly Gln
        355                 360                 365

Trp Glu Arg Ala Gln Arg Glu Gln Ala Gln Thr Ala Arg Gly Leu Gln
    370                 375                 380

Glu Leu Arg Gly Arg Ala Asp Glu Leu Cys Thr Met Val Glu Arg Ser
385                 390                 395                 400

Ala Val Ser Val Ala Ser Leu Arg Ser Glu Leu Glu Gly Leu Gly Pro
                405                 410                 415

Leu Lys Pro Ile Leu Glu Glu Phe Gly Arg Gln Phe Gln Asn Ser Arg
            420                 425                 430

Arg Gly Pro Asp Leu Ser Met Asn Leu Asp Arg Ser His Gln Gly Asn
        435                 440                 445

Cys Ala Arg Cys Ala Ser Gln Gly Ser Gln Leu Ser Thr Glu Ser Leu
    450                 455                 460

Gln Gln Leu Leu Asp Arg Ala Leu Thr Ser Leu Val Asp Glu Val Lys
465                 470                 475                 480

Gln Arg Gly Leu Thr Pro Ala Cys Pro Ser Cys Gln Arg Leu His Lys
                485                 490                 495

Lys Ile Leu Glu Leu Glu Arg Gln Ala Leu Ala Lys His Val Arg Ala
            500                 505                 510

Glu Ala Leu Ser Ser Thr Leu Arg Leu Ala Gln Asp Glu Ala Leu Arg
        515                 520                 525

Ala Lys Asn Leu Leu Leu Thr Asp Lys Met Lys Pro Glu Glu Lys Met
    530                 535                 540

Ala Thr Leu Asp His Leu His Leu Lys Met Cys Ser Leu His Asp His
545                 550                 555                 560

Leu Ser Asn Leu Pro Leu Glu Gly Ser Thr Gly Thr Met Gly Gly Gly
                565                 570                 575

Ser Ser Ala Gly Thr Pro Pro Lys Gln Gly Gly Ser Ala Pro Glu Gln
            580                 585                 590
```

-continued

SEQ ID NO 9
LENGTH: 268
TYPE: PRT
ORGANISM: Mus musculus

SEQUENCE: 9

Met Glu Asp Phe Leu Leu Ser Asn Gly Tyr Gln Leu Gly Lys Thr Ile
1               5                   10                  15

Gly Glu Gly Thr Tyr Ser Lys Val Lys Glu Ala Phe Ser Lys Lys His
            20                  25                  30

Gln Arg Lys Val Ala Ile Lys Ile Ile Asp Lys Met Gly Gly Pro Glu
        35                  40                  45

Glu Phe Ile Gln Arg Phe Leu Pro Arg Glu Leu Gln Ile Val Arg Thr
    50                  55                  60

Leu Asp His Lys Asn Ile Ile Gln Val Tyr Glu Met Leu Glu Ser Ala
65                  70                  75                  80

Asp Gly Lys Ile Tyr Leu Val Met Glu Leu Ala Glu Gly Gly Asp Val
                85                  90                  95

Phe Asp Cys Val Leu Asn Gly Gly Pro Leu Pro Glu Ser Arg Ala Lys
            100                 105                 110

Ala Leu Phe Arg Gln Met Val Glu Ala Ile Arg Tyr Cys His Gly Cys
        115                 120                 125

Gly Val Ala His Arg Asp Leu Lys Cys Glu Asn Ala Leu Leu Gln Gly
    130                 135                 140

Phe Asn Leu Lys Leu Thr Asp Phe Gly Phe Ala Lys Val Leu Pro Lys
145                 150                 155                 160

Ser Arg Arg Glu Leu Ser Gln Thr Phe Cys Gly Ser Thr Ala Tyr Ala
                165                 170                 175

Ala Pro Glu Val Leu Gln Gly Ile Pro His Asp Ser Lys Lys Gly Asp
            180                 185                 190

Val Trp Ser Met Gly Val Val Leu Tyr Val Met Leu Cys Ala Ser Leu
        195                 200                 205

Pro Phe Asp Asp Thr Asp Ile Pro Lys Met Leu Trp Gln Gln Gln Lys
    210                 215                 220

Gly Val Ser Phe Pro Thr His Leu Gly Ile Ser Thr Glu Cys Gln Asp
225                 230                 235                 240

Leu Leu Lys Arg Leu Leu Glu Pro Asp Met Ile Leu Arg Pro Ser Ile
                245                 250                 255

Glu Glu Val Ser Trp His Pro Trp Leu Ala Ser Thr
            260                 265

<210> SEQ ID NO 10
<211> LENGTH: 1020
<212> TYPE: DNA
<213> ORGANISM: Mus musculus

<400> SEQUENCE: 10
gcacgagatg ttctagccct ggaggcagct gtgaatgaag tccttggggg gaaaagaagc      60
aggccgaggg cgatggtgga gtagagctgc ctcgcagagg cagcatgagc tgagagggtg     120
acaagaagga ggcgctacac agcatggagg actttctact ctccaatggg tatcagctgg     180
gcaagaccat tggggaaggg acctactcaa aagtcaaaga agcattttcc aaaaaacatc     240
aacgaaaagt ggcaattaaa attatagaca agatgggagg gccagaagag tttatccaga     300
gattcctgcc tcgtgagctc cagattgtcc gtaccctgga ccacaaaaac atcatccagg     360
tgtatgagat gctggagtca gcagatggaa aaatctacct ggtgatggag ctggctgagg     420

```
gaggggatgt ctttgactgt gtgctgaacg gagggccact tcccgagagc cgggccaagg      480
ccctcttccg ccagatggtt gaggctattc gctattgcca tggctgtggc gtggcccacc      540
gggaccttaa gtgtgagaac gccttgttgc agggcttcaa cctgaagctg accgactttg      600
gctttgccaa ggtgctaccc aagtcacgca gggagctgag ccagaccttc tgtggcagca      660
cagcctatgc cgcccctgag gtgctacagg gcataccccca tgatagcaag aaaggtgatg     720
tctggagcat gggtgtggtc ctgtatgtaa tgctctgtgc aagtctacct tttgacgaca      780
cagatatccc caagatgctg tggcagcagc agaagggggt gtccttcccc actcatttgg      840
gcatctcaac cgaatgccag gacctgctca gcggctcct ggaaccagac atgatactcc       900
ggccttcaat cgaagaagtt agttggcacc catggctagc aagcacttga taaaagcaat      960
ggcaagtcct ccccaataaa gtaggggag aaagcaaact gaaaaaaaaa aaaaaaaaa       1020
```

<210> SEQ ID NO 11
<211> LENGTH: 24
<212> TYPE: DNA
<213> ORGANISM: synthetic construct
<220> FEATURE:
<221> NAME/KEY: primer_bind
<222> LOCATION: (1)..(24)
<223> OTHER INFORMATION:

<400> SEQUENCE: 11
cgtggatcca waggaccasa crtc                                              24

<210> SEQ ID NO 12
<211> LENGTH: 20
<212> TYPE: DNA
<213> ORGANISM: synthetic construct
<220> FEATURE:
<221> NAME/KEY: primer_bind
<222> LOCATION: (1)..(20)
<223> OTHER INFORMATION: The n at position 15 represents any nucleotide
      selected from a, t, c, or g.
<220> FEATURE:
<221> NAME/KEY: misc_feature
<222> LOCATION: (15)..(15)
<223> OTHER INFORMATION: The n at position 15 represents any
      nucleotide selected from a, t, c, or g.

<400> SEQUENCE: 12
attcggatcc acmgngayyt                                                   20

<210> SEQ ID NO 13
<211> LENGTH: 24
<212> TYPE: DNA
<213> ORGANISM: synthetic construct
<220> FEATURE:
<221> NAME/KEY: primer_bind
<222> LOCATION: (1)..(24)
<223> OTHER INFORMATION:

<400> SEQUENCE: 13
catcaccttt cttgctatca tggg                                              24

<210> SEQ ID NO 14
<211> LENGTH: 21
<212> TYPE: DNA
<213> ORGANISM: synthetic construct
<220> FEATURE:
<221> NAME/KEY: primer_bind

```
<222> LOCATION: (1)..(21)
<223> OTHER INFORMATION:

<400> SEQUENCE: 14
tgtgagaacg ccttgttgca g                                              21

<210> SEQ ID NO 15
<211> LENGTH: 23
<212> TYPE: DNA
<213> ORGANISM: synthetic construct
<220> FEATURE:
<221> NAME/KEY: primer_bind
<222> LOCATION: (1)..(23)
<223> OTHER INFORMATION:

<400> SEQUENCE: 15
gacatcacct tttttgctat cgt                                            23

<210> SEQ ID NO 16
<211> LENGTH: 27
<212> TYPE: DNA
<213> ORGANISM: synthetic construct
<220> FEATURE:
<221> NAME/KEY: primer_bind
<222> LOCATION: (1)..(27)
<223> OTHER INFORMATION:

<400> SEQUENCE: 16
ccatcctaat acgactcact atagggc                                        27

<210> SEQ ID NO 17
<211> LENGTH: 24
<212> TYPE: DNA
<213> ORGANISM: synthetic construct
<220> FEATURE:
<221> NAME/KEY: primer_bind
<222> LOCATION: (1)..(24)
<223> OTHER INFORMATION:

<400> SEQUENCE: 17
gcaggtgaga atgttctaac gctg                                           24

<210> SEQ ID NO 18
<211> LENGTH: 24
<212> TYPE: DNA
<213> ORGANISM: synthetic construct
<220> FEATURE:
<221> NAME/KEY: primer_bind
<222> LOCATION: (1)..(24)
<223> OTHER INFORMATION:

<400> SEQUENCE: 18 tctccccta ctttattgga gagc                                            24
```